United States Patent [19]

Yoshinaga et al.

[11] Patent Number: 4,946,855
[45] Date of Patent: Aug. 7, 1990

[54] CARBOXAMIDE DERIVATIVES HAVING TETRAZOLE AND THIAZOLE RINGS AND THEIR USE

[75] Inventors: Junji Yoshinaga, Neyagawa; Takeshi Shogaki, Suita; Takao Kakita, Toyonaka; Hiromi Ozeki, Osaka; Yoshiko Kato, Nishinomiya, all of Japan

[73] Assignee: Sawai Pharmaceutical Co., Ltd., Osaka, Japan

[21] Appl. No.: 276,953

[22] Filed: Nov. 28, 1988

[30] Foreign Application Priority Data

Dec. 14, 1987 [JP] Japan .................. 62-318211
Mar. 9, 1988 [JP] Japan .................. 63-055583
Apr. 15, 1988 [JP] Japan .................. 63-093686

[51] Int. Cl.$^5$ .................. C07D 417/12; C07D 417/44; A61K 31/425
[52] U.S. Cl. .................. 514/371; 514/314; 514/342; 546/167; 546/276; 548/195
[58] Field of Search .............. 548/195; 514/371, 314, 514/342; 546/167, 276

[56] References Cited

U.S. PATENT DOCUMENTS

| | | | |
|---|---|---|---|
| 4,112,106 | 9/1978 | Sellstedt | 548/194 |
| 4,146,631 | 3/1979 | Ford et al. | 514/371 |
| 4,225,610 | 9/1980 | Tarayre et al. | 514/371 |
| 4,432,986 | 2/1984 | Erickson | 514/371 |
| 4,526,979 | 7/1985 | Peet et al. | 514/371 |
| 4,558,059 | 12/1985 | Kawasaki et al. | 514/371 |
| 4,567,193 | 1/1986 | Peet et al. | 514/371 |

FOREIGN PATENT DOCUMENTS

| | | | |
|---|---|---|---|
| 0051409 | 5/1982 | European Pat. Off. | 514/371 |
| 0209234 | 1/1987 | European Pat. Off. | 514/371 |
| 0262873 | 9/1987 | European Pat. Off. | 548/193 |
| 8099 | 3/1973 | Japan | 514/371 |
| 167685 | 7/1986 | Japan | 514/371 |
| 2006782 | 5/1979 | United Kingdom | 514/371 |

OTHER PUBLICATIONS

J. Med. Chem. 26, pp. 1499–1504 (1983).
Chem. Abst. 79, (15), pp. 441, No. 92204b.
J. Med. Chem. 26, pp. 1158–1163 (1983).
J. Med. Chem. 29, pp. 538–549 (1986).
J. Med. Chem. 29, pp. 2403–2409 (1986).

*Primary Examiner*—Robert Gerstl
*Attorney, Agent, or Firm*—Scully, Scott, Murphy & Presser

[57] ABSTRACT

A compound of the formula:

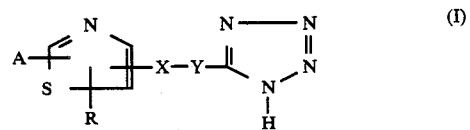

wherein
the free valency of the groups A-, R- and —X—Y— is attached to any of 2-, 4- and 5- positions of the thiazol ring, A is a $C_{1-6}$ alkyl group, an aryl group which is unsubstituted or substituted with at least one substituent selected from the group consisting of hydroxy $C_{1-6}$ alkoxy, aryl-($C_{1-6}$)alkoxy, halo-($C_{1-6}$)alkyl, halogen, and nitro,
or 5- or 6-membered heterocyclic group containing at least one hetero atom selected from oxygen, nitrogen and sulfur, or a condensed heterocyclic group consisting of a heterocycle as defined above and a benzene nucleus, these two heterocyclic groups being unsubstituted or substituted with at least one substituent selected from halogen,
R is hydrogen or a $C_{1-6}$alkyl group,
X is —CO—or —NH—, and
Y is —NH—or —CO—, with the proviso that
(a) X and Y cannot be the same group, and
(b) when X is —CO—and Y is —NH—, the group —X—Y—is attached to 2- or 5-position,
or a pharmaceutically acceptable salt thereof are nobel and useful as antiallergic.

12 Claims, No Drawings

CARBOXAMIDE DERIVATIVES HAVING TETRAZOLE AND THIAZOLE RINGS AND THEIR USE

BACKGROUND OF THE INVENTION

1. FIELD OF THE INVENTION

The present invention relates to carboxamide derivatives having tetrazolyl and thiazole rings, a process for preparation thereof, a pharmaceutical composition comprising the said derivatives and use thereof as antiallergic.

Various compounds including disodium cromoglicate, chlorpheniramine maleate, tranilast etc. have been known to have the antiallergic activity and practically used on the basis of such activity. However, they have a number of deficiencies such as induction of undesirable side effects, insufficiency of peroral absorption and unsatisfactoriness of therapeutic effect. Accordingly, there has been a continuous demand for antiallergic agent which has not such deficiencies.

After an extensive study on the antiallergic agents, the present inventors have discovered that a certain group of carboxamide derivatives having tetrazolyl and thiazole rings have an excellent antiallergic activity even if they administered perorally and have less side effects.

2. RELATED DISCLOSURES

N-substituted phenylthiazolecarboxamide derivatives wherein the substituents are alkyl, aryl, alicyclic or benzyl are disclosed in Japanese Patent Publication No. 8099/1973 (JP=Bl), EP-A-0051409, Chem. Abst. 79, 92204b and U.S. Pat. No. 4558059. N-thiazolyl oxamic acid derivatives are disclosed in J. Med. Chem. 26, 1158–1163(1983). N-tetrazolyl benzamides are disclosed in U.S. Pat. Nos. 4526979, 4567193 and 4146631, J. Med. Chem. 29, 538–549(1986) and ibid, 29, 2403–2409(1986). N-teterazolyl nicotinamides are disclosed in J. Med. Chem. 26, 1499–1504(1983). N-tetrazolyl aromatic carboxamides are disclosed in U.S. Pat. No. 4,432,986. Thiazolylmethyl tetrazoles are disclosed in Japanese Patent Publication (Unexamined) No. 167685/1986 (JP=A).

SUMMARY OF THE INVENTION

In one aspect, the present invention relates to a compound of the formula:

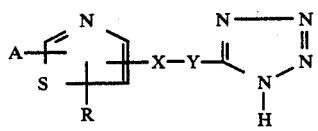

wherein the free valency of the groups A—, R— and —X—Y— is attached to any of 2-, 4- and 5-positions of the thiazole ring, A is a $C_{1-6}$ alkyl group, an aryl group which is unsubstituted or substituted with at least one substituent selected from the group consisting of hydroxy, $C_{1-6}$ alkoxy, aryl-($C_{1-6}$)alkoxy, halo-($C_{1-6}$)alkyl, halogen, and nitro, or 5- or 6-membered heterocyclic group containing at least one hetero atom selected from oxygen, nitrogen and sulfur, or a condensed heterocyclic group consisting of a heterocycle as defined above and a benzene nucleus, these two heterocyclic groups being unsubstituted or substituted with at least one substituent selected from halogen, R is hydrogen or a $C_{1-6}$ alkyl group, X is —CO— or —NH—, and Y is —NH— or —CO—, with the proviso that (a) X and Y cannot be the same group, and (b) when X is —CO— and Y is —NH—, the group —X—Y— is attached to 2- or 5-position, or a pharmaceutically acceptable salt thereof.

The compounds of the above formula (I) may be prepared by the following processes:

(Process a) reacting a carboxylic acid of the formula:

wherein

A and R are as defined in claim 1, with the proviso that —COOH is attached to 2- or 5-position of the thiazole ring, or a reactive derivative at the carboxy group thereof, with an amine of the formula:

or a reactive derivative at the amino group thereof, to give a compound of formula (I) wherein X is —CO— and Y is —NH—, or (Process b) reacting a carboxylic acid of the formula:

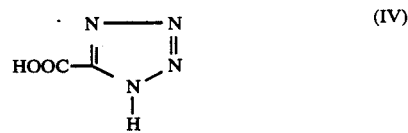

or a reactive derivative at the carboxy group thereof, with an amine of the formula:

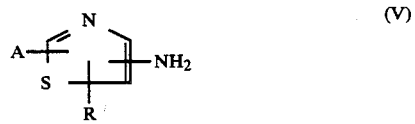

wherein A and R are as defined above, or a reactive derivative at the amino group thereof, to give a compound of formula (I) wherein X is —NH— and Y is —CO—.

In another aspect, the present invention relates to a pharmaceutical composition, useful in treatment of allergic diseases, comprising as an active ingredient the compound of the above formula (I) or a pharmaceutically acceptable salt thereof in association with a pharmaceutically acceptable carrier, diluent or excipient.

In a further aspect, the present invention provides a use of the compound of the above formula (I) or a pharmaceutically acceptable salt thereof for the manufacture of a medicament for treatment of allergic diseases.

In a still further aspect, the present invention provides a method of treating allergic diseases which comprises administering a therapeutically or prophylactically effective amount of the compound of the above formula (I) or a pharmaceutically acceptable salt thereof to a subject in need of such treatment.

DETAILED DESCRIPTION OF THE INVENTION

DEFINITIONS

The terms and the definitions described in this specification are illustrated in more detail as follows:

The term "$C_{1-6}$alkyl" as a group or a moiety in halo-($C_{1-6}$)alkyl includes saturated straight or branched chain hydrocarbon radicals containing the number of (preferredly 1-5 and more preferredly 1-4) carbon atoms indicated, such as methyl, ethyl, propyl, isopropyl, butyl, isobutyl, t-butyl, pentyl and hexyl. The term "$C_{1-6}$alkoxy" as a group or a moiety in aryl-($C_{1-6}$)alkoxy refers to the group-O-($C_{1-6}$)alkyl wherein ($C_{1-6}$)alkyl is as defined above.

The term "halo" as a radical or a moiety in halo-($C_{1-6}$)alkyl denotes fluoro, chloro, bromo and iodo.

The term "halo-($C_{1-6}$)alkyl" includes $C_{1-6}$ alkyl substituted at least with one, usually 1 to 5 and preferredly 1 to 3 halogen atoms, such as chloromethyl, trifluoromethyl and 2,2,2,-trichloroethyl.

The term "aryl" as a group or a moiety in aryl-($C_{1-6}$)alkoxy includes monocyclic aryl such as unsubstituted phenyl and $C_{1-6}$ alkylphenyl wherein $C_{1-6}$ alkyl is as defined above (such as tolyl, xylyl, cumenyl etc.) and bicyclic aryl such as biphenylyl and naphthyl unsubstituted or substituted with $C_{1-6}$ alkyl wherein $C_{1-6}$ alkyl is as defined above. These aryl may be unsubstituted or substituted with at least one, usually 1 to 5 and preferredly 1 to 3 substituents selected form hydroxy, $C_{1-6}$alkoxy (e.g. $CH_3O$—, $C_2H_5O$— or t—$C_4H_9O$—), aryl-($C_{1-6}$)alkoxy (e.g. $C_6H_5CH_2O$—), halo-($C_{1-6}$)alkyl (e.g. $CF_3$—), halogen (e.g. Cl— or Br—) and nitro. When the aryl has two or more substituents, they may be the same or different.

The term "5- or 6-membered heterocyclic group containing at least one hetero atom selected from oxygen, nitrogen and sulfur" includes 5-membered heterocyclic groups containing at 1,2,3,4, or more hetero atoms as defined above, such as furyl, thienyl, pyrrolyl, imidazolyl, oxazolyl, thiazolyl, triazolyl, tetrazolyl etc. and 6-membered heterocyclic groups containing 1,2,3,4 or more hetero atom as defined above, such as pyridyl, pyrazinyl, pyridazinyl, oxazinyl, thiazinyl, triazinyl etc.

The term "condensed heterocyclic group consisting of a heterocyclic group as defined above and a benzene nucleus" includes condensed heterocyclic groups consisting of the 5-membered heterocyclic group as defined above and a benzene nucleus, such as indolyl, indazolyl etc. and condensed heterocyclic groups consisting of the 6-membered heterocyclic group as defined above and a benzene nucleus, such as quinolyl, isoquinolyl, quinazolinyl, benzothiazinyl etc.

The above defined heterocyclic groups may be unsubstituted or substituted with at least one, usually 1 to 5 and preferredly 1 to 3 substituents selected from halogen (e.g. Cl— or Br—). When the heterocyclic groups have two or more substituents, they may be the same or different.

The 1H-tetrazolyl group of the formula:

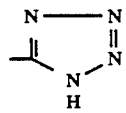

is well known to lie in tautomeric relation with a 2H-tetrazolyl group of the formula:

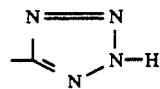

Accordingly, it is to be understood that both of the said groups are substantially the same, and the tautomers consisting of such groups are regarded as the same compounds. Therefore, both of the tautomeric forms of the compounds having such groups in their molecule are included in the scope of this invention and designated inclusively with one expression "1H-tetrazolyl" only for the convenient sake throughout this specification.

Suitable "pharmaceutically acceptable salt" includes conventional non-toxic salt, and may be a salt with an inorganic base, for example, a metal salt such as an alkali metal salt (e.g. sodium salt, potassium salt, etc.) and an alkaline earth metal salt (e.g. calcium salt, magnesium salt, etc.), ammonium salt, a salt with an organic base, for example, an amine salt (e.g. trimethylamine salt, triethylamine salt, procaine salt, dicyclohexylamine salt, N,N'-dibenzylethylenediamine salt, N-methylglucamine salt, monoethanolamine salt, diethanolamine salt, triethanolamine salt, tris(hydroxymethylamino)methane salt, phenethylbenzylamine salt, etc.), a basic amino acid salt (e.g. arginine salt, lysine salt, etc.) and the like. These salts can be prepared by the conventional process, for example from the corresponding acid and base or by salt interchange.

One class of the compounds of the formula (I) are those represented by the formula:

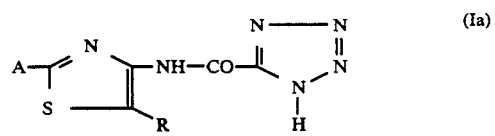

(Ia)

wherein

A is a $C_{1-6}$ alkyl group, an aryl group which is unsubstituted or substituted with at least one substituent selected from the group consisting of hydroxy, $C_{1-6}$alkoxy, aryl-($C_{1-6}$)alkoxy, halo-($C_{1-6}$)alkyl, halogen, and nitro, or 5- or 6-membered heterocyclic group containing at least one hetero atom selected from oxygen, nitrogen and sulfur, or a condensed heterocyclic group consisting of a heterocycle as defined above and a benzene nucleus, these two heterocyclic groups being unsubstituted or substituted with at least one substituent selected from halogen, R is hydrogen or a $C_{1-6}$alkyl group.

Preferred compounds within this class are those wherein

A is methyl, phenyl, methylphenyl, (1-methylethyl)phenyl, (1,1-dimethylethyl)phenyl, naphthyl, hydroxyphenyl, methoxyphenyl, dimethoxyphenyl, trimethoxyphenyl, benzyloxyphenyl, trifluoromethylphenyl, chlorophenyl, nitrophenyl, pyridyl, furyl, thienyl, or quinolyl and R is hydrogen, methyl or 1-methylethyl.

Another class of the compounds of the formula (I) are those represented by the formula:

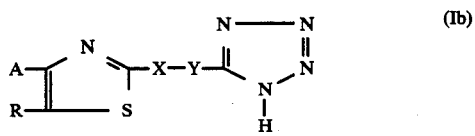

wherein

A is an aryl group which is unsubstituted or substituted with at least one substituent selected from the group consisting of $C_{1-6}$alkoxy, aryl-($C_{1-6}$)alkoxy, halo-($C_{1-6}$)alkyl, halogen, and nitro, or 5-membered heterocyclic group containing at least one hetero atom selected from oxygen, nitrogen and sulfur, the heterocyclic group being unsubstituted or substituted with at least one substituent selected from halogen, R is hydrogen or a $C_{1-6}$alkyl group, X is —CO— or —NH—, and Y is —NH— or —CO—, with the proviso that (a) X and Y cannot be the same group.

Preferred compounds within this class are those wherein

A is phenyl, methylphenyl, ethylphenyl, dimethylphenyl, biphenylyl, naphthyl, methoxyphenyl, dimethoxyphenyl, benzyloxyphenyl, chlorophenyl, trichlorophenyl, trifluoromethylphenyl, nitrophenyl, pyridyl, furyl, thienyl, or chlorothienyl, and R is hydrogen or methyl.

A further class of the compounds of the formula (I) are those represented by the formula:

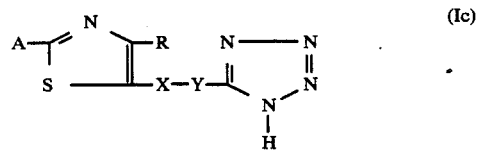

wherein

A is an aryl group which is unsubstituted or substituted with at least one substituent selected from the group consisting of $C_{1-6}$alkoxy, halogen and nitro, R is $C_{1-6}$ alkyl group, X is —CO— or —NH—, and Y is —NH— or —CO—, with the proviso that (a) X and Y cannot be the same group.

Preferred compounds within this class are those wherein A is phenyl, methylphenyl, methoxyphenyl, dimethoxyphenyl, trimethoxyphenyl, chlorophenyl, or nitrophenyl, and R is methyl.

PREPARATION

The process for preparing the compound (I) is explained in details in the following.

(Process a) The compound (I) can be obtained by reacting the compound (II) or a reactive derivative at the carboxy group thereof with the compound (III) or a reactive derivative at the amino group thereof.

(Process b) Alternatively, the compound (I) can be obtained by reacting the compound (IV) or a reactive derivative at the carboxy group thereof with the compound (V) or a reactive derivative at the amino group thereof.

The reactive derivative at the carboxy group of the compound (II) or (IV) includes acid halides, acid anhydrides, activated esters and activated amides. Among the acid halides, acid chloride is the most frequently used. Examples of the acid anhydrides include dialkylphosphoric acid mixed anhydride, dialkylphosphorous acid mixed anhydride, alkylcarbonic acid mixed anhydride, aliphatic carboxylic acid (e.g. pivalic acid, trichloroacetic acid) mixed anhydride etc. Examples of the activated esters include methyl ester, ethyl ester, cyanomethyl ester, p-nitrophenyl ester, an ester with N-hydroxysuccinimide etc. Examples of the activated amides include an amide with imidazole, dimethylimidazole or triazole.

The reactive derivative at the amino group of the compound (III) or (V) includes a Schiff's base with an aldehyde (e.g. acetaldehyde, isopentanal, benzaldehyde), a reaction product with a silyl compound (e.g. trimethylsilyl chloride, trimethylsilylacetamide), a reaction product with a phosphorus compound (e.g. phosphorus trichloride, phosphorus oxychloride).

When the compound (I) or (IV) is used in the form of carboxylic acid, it is advantageous to carry out the reaction in the presence of condensing agent which may be any one conventionally used in the peptide synthesis. Examples of the condensing agent include halogenating agents such as $SOCl_2$, $SO_2Cl_2$, $PCl_3$, $PCl_5$, $POCl_3$, $PBr_3$, or N,N'-dicyclohexyl carbodiimide (DCC), N-cyclohexyl-N'-morpholinoethyl carbodiimide, N,N'-diisopropyl carbodiimide, $ClCO_2CH_3$, $ClCO_2C_2H_5$, $BrCO_2CH_3$, $(CH_3CO)_2O$, N-ethylbenzisoxazolium salts, 2-chloro-1-methylpyridinium salt, N,N'-carbonyl diimidazole (CDI), etc.

The reaction may be carried out without the solvent but is usually carried out in an inert solvent. Examples of the solvent include dioxane, methylene chloride, chloroform, ether, tetrahydrofuran (THF), acetone, dimethylformamide (DMF), dimethylsulfoxide (DMSO), pyridine, acetonitrile, benzene, toluene xylene etc.

A preferred example of operation is as follows.

The acid (II) or (IV) is dissolved in an inert solvent and a condensing agent is added thereto. When the condensing agent is a halogenating agent, the addition is preferably carried out under ice-cooling, while other agent may be added either under ice-cooling or without cooling (i.e., at ambient temperature). The reaction mixture is kept at ambient temperature or elevated temperature such as reflux point for 0.5-3 hours. Then the activated acid thus formed is treated with the amine (III) or (V) with or without isolation. This reaction may be conducted in an inert organic solvent and, if necessary, in the presence of a base to form the desired compound (I). The base may be any one which can capture hydrogen halide, such as a tertiary amine (e.g. triethylamine, dimethylaniline or pyridine) and the amine (III) or (V) can also serve as the base. The inert solvent may be the same as that used in the former step. A satisfactory yield can be obtained when the reaction is carried out at a temperature from ambient temperature up to the boiling temperature of the solvent for 0.5–5 hours.

Some of the starting compounds are novel and can be prepared by the following process.

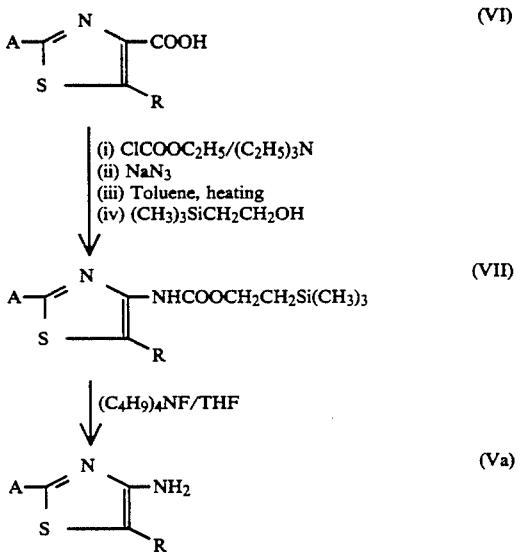

Briefly, the compound (VI) are reacted with a haloformate (e.g., ethyl chlorioformate) to form a reactive derivative of the carboxylic acid (VI). The reactive derivative is converted to a carbonylazide by treating with sodium azide. The carbonylazide is converted to isocyanate when heated under reflux in toluene, and then trimethylsilylethanol is added to the isocyanate under reflux in toluene. The formed 2-trimethylsilylester is treated with tetrabutylammonium fluoride in THF solution to give the compound (Va).

Tetrazole-5-carboxylic acid can be prepared by treating ethyl cyanoformate with sodium azide and ammonium chloride to form ethyl tetrazole-5-carboxylate, which is hydrolyzed with alkali (e.g., KOH) to give alkali tetrazole-5-carboxylate, according to the method described in J. Med. Chem. 19, 289(1976) and Ibid, 29, 538(1986).

2-Amino-4-A-5-R-thiazole can be prepared by the method described in U.S. Pat. No. 4,246,271 (A).

4-A-5-R-2-thiazolecarboxylic acid or 2-A-4-R-5-thiazolecarboxylic acid can be obtained according to the method described in Chem. Abst. 64, 724a(1966) and DE 2045818 Al.

ADMINISTRATION

The compound (I) of the present invention has a potent antiallergic activity and therefore useful as a medicament for preventing or treating allergic diseases.

For prophylactic and/or therapeutic administration, the compound (I) of the present invention is used in the form of conventional pharmaceutical preparation which contains said compound, as an active ingredient, in admixture with pharmaceutically acceptable carriers such as an organic or inorganic solid or liquid excipient which is suitable for oral parenteral or external administration. The pharmaceutical preparations may be in solid form such as capsule, tablet, dragee, ointment or suppository, or in liquid form such as solution, suspension, or emulsion. If needed, there may be included in the above preparations auxiliary substances, stabilizing agents, wetting or emulsifying agents, buffers and the other commonly used additives.

While the dosage of the compound (I) may vary from and also depend upon the age and conditions of the patient, a kind and degree of disease, and further a kind of the active compound (I) to be applied, an average single dose of about 0.5–50 or 100 mg/kg of the active compound (I) conveniently administered in 2–4 divided dosages a day or in a sustained release form is sufficient for treating allergic diseases.

Following preparations and examples are given only for explanation of this invention in more detail.

EXAMPLE

The present invention will now be further illustrated by reference to the following various examples, which are not, however, intended to limit the scope of the invention.

Preparation 1

2-Methyl-4-thiazolamine(Va-1)(synthesis of starting material)

To a solution of 2-methyl-4-thiazolecarboxylic acid (1.80 g, 12.57 mmol) dissolved in dry tetrahydrofuran (25 ml) was added dropwise triethylamine (1.75 ml, 12.57 mmol). After adding ethyl chlorocarbonate (1.20 ml, 12.57 mmol) dropwise in an ice-salt bath, the mixture was allowed to react under the same conditions for 15 minutes. The reaction mixture was transferred to an ice bath. An aqueous solution (40 ml) of sodium azide (6.32 g,.94.29 mmol) was added thereto and the mixture was allowed to react under the same conditions for 30 minutes. After addition of water, the reaction mixture was extracted with ethyl acetate. The organic layer was washed with saturated saline and dried over anhydrous sodium sulfate. The solvent was distilled off to give carbonylazide (1.88 g) as pale yellow solids. These were suspended in dry toluene (25 ml) under argon and allowed to react at 90° C. for 50 minutes. Under the same conditions, 2-trimethylsilylethanol (3.21 ml, 22.4 mmol) was added thereto and the mixture was allowed to react for additional 1.5 hours. Then the solvent was removed from the reaction mixture and the residue was dissolved in benzene and purified by silica gel column (hexane:ethyl acetate=7:3) to give 1.456 g of 2-trimethylsilylethyl 2-methyl-4-thiazolecarbamate (m.p. 101°–103° C.) as white solids. These white solids were dissolved in 1M solution of tetrabutylammouinm fluoride in tetrahydrofuran (22.53 ml, 22.53 mmol) and allowed to react at 50°–60° C. for 25 minutes. The solvent was removed from the reaction mixture and the residue was treated with water and extracted with ethyl acetate. The organic layer was washed with saturated ammonium chloride solution followed by saturated saline, and then dried over anhydrous sodium sulfate. The solvent was distilled off to give 447.8 mg or 2-methyl-4-thiazolamine (yield 31%) as brown oil.

Preparation 2

2-(4-Methylphenyl)-4-thiazolamine(Va-5) (synthesis of starting material)

To a solution of 2-(4-methylphenyl)-4-thiazolecarboxylic acid (1 g, 4.56 mmol) dissolved in dry tetrahydrofuran (13 ml) was added dropwise triethylamine (0.64 ml, 4.56 mmol). After adding ethyl chlorocarbonate (0.44 ml, 4.56 mmol) dropwise in an ice-salt bath, the mixture was allowed to react under the same conditions for 15 minutes. The reaction mixture was transferred to an ice bath. An aqueous solution (15 ml) of sodium azide (2.22 g, 34.21 mmol) was added thereto and the mixture was allowed to react under the same conditions for 30 minutes. After addition of water, the reaction mixture was extracted with ethyl acetate. The organic layer was washed with saturated saline and dried over anhydrous sodium sulfate. The solvent was distilled off to give carbonylazide (995.1 mg) as pale yellow solids. These were suspended in dry toluene (12 ml) under argon and allowed to react at 90° C. for 40 minutes. Under the same conditions, 2-trimethylsilylethanol (1.17 ml, 8.15 mmol) was added thereto and allowed to react for additional 1.5 hours. Then the solvent was removed from the reaction mixture and the residue was dissolved in benzene and purified by silica gel column (hexane:ethyl acetate=9:1). The second fraction was collected and the solvent was distilled off from the fraction to give 1.110 g of 2-trimethylsilylethyl 2-(4-methylphenyl)-4-thiazolecarbamate (m.p. 108°–109° C.) as pale yellow solids. These solids were dissolved in 1M solution of tetrabutylammouium fluoride in tetrahydrofuran (11.36 ml, 11.3 mmol) and allowed to react at 60° C. for 30 minutes. The solvent was removed from the reaction mixture, and the residue was treated with water and extracted with ethyl acetate. The organic layer was washed with saturated ammonium chloride solution followed by saturated saline, and then dried over anhydrous sodium sulfate. The solvent was removed to give 547.2 mg of 2-(4-methylphenyl)-4-thiazolamide (yield 73%) as yellow solids. These solids were recrystallized from n-hexane to give yellow needles, m.p. 100°–102° C.

Preparation 3

2-(3-Pyridinyl)-4-thiazolamine(Va-23) (synthesis of starting material)

To a suspension of 2-(3-pyridinyl)-4-thiazolecarboxylic acid (1.5 g, 7.28 mmol) in dry tetrahydrofuran (30 ml) was added dropwise triethylamine (2.03 ml, 14.56 mmol) and then ethyl chlorocarbonate (0.692 ml, 7.28 mmol) in an ice-salt bath and allowed to react under the same conditions for 20 minutes. The reaction mixture was transferred to an ice bath. After adding an aqueous solution (20 ml) of sodium azide (4.7 g, 7.28 mmol), the mixture was allowed to react under the same conditions for 10 minutes. The reaction mixture was treated with water and extracted with ethyl acetate, and then the organic layer was washed with saturated saline and dried over anhydrous sodium sulfate. The solvent was distilled off to give carbonylazide (1.23 g) as yellow solids. These were dissolved in dry toluene (30 ml) under argon and allowed to react at 90° C. for 1 hour. Under the same conditions, 2-trimethylsilylethanol (1.54 ml, 10.64 mmol) was added thereto and the mixture was allowed to react for additional 1.5 hours. After addition of water the reaction mixture was extracted with ethyl acetate, and the organic layer was washed with water and then dried over anhydrous sodium sulfate. After the solvent was distilled off, the residue was dissolved in 30 ml of developing solvent (chloroform:ethyl acetate=6.4). The insoluble matters in the reaction mixture were collected by filteraction and dried to give 870 mg of 2-trimethylsilylethyl-2-(3-pyridyl)-4-thiazolecarbamate as pale yellow solids. The filtrates were purified by silica gel column (chloroform:ethyl acetate=6:4), the first fraction was collected and the solvent was distilled off from the fraction to give 1.216 g (combined with the above obtained solid, yield 52%, m.p. 172°–175° C.). The combined yellow solids (1.1 g, 3.42 mmol) was suspended in dry tetrahydrofuran (10 ml). After dissolution was effected with addition of 1M solution of tetrabutylammonium fluoride in tetrahydrofuran (13.68 ml, 13.68 mmol), the mixture was allowed to react at 50° C. for 15 minutes. The solvent was distilled off from the reaction mixture and the residue was treated with water and extracted with ethyl acetate. The organic layer was washed with saturated ammonium chloride solution followed by saturated saline, and then dried over anhydrous sodium sulfate. The solvent was distilled off to give 738 mg (yield 52%) of 2-(3-pyridyl)-4-thiazolamine as dark brown viscous oil, which was recrystallized from n-hexane-benzene to form yellow crystals, m.p. 71°–73° C.

EXAMPLE 1

N-(2-Methyl-4-thiazolyl)-1H-tetrazole-5-carboxamide (Ia-1) (Process b)

A mixture, obtained by adding dry DMF(0.43 ml, 5.55 mmol) and then thionyl chloride (0.405 ml, 5.55 mmol) to dry benzene (1 ml) under ice-cooling, was allowed to warm up to room temperature and to react for. 10 minutes upon which the mixture separated into two layers. The lower layer was added dropwise to dipotassium salt of 1H-tetrazole-5-carboxylic acid (704 mg, 3.70 mmol) suspended in dry acetonitrile (9 ml) under ice-cooling, and the mixture was allowed to react for 15 minutes. After adding dropwise a mixed solution of 2-methyl-4-thiazolamine (447.8 mg, 3.92 mmol) in dry acetonitrile (5 ml) and dry pyridine (1 ml) under the same conditions, the mixture was allowed to warm up to room temperature and to react for 1 hour. To the reaction mixture was added water, and the insoluble solids was removed by filtration and the filtrate was acidified with ice-cooled 2N HCl to pH 2. The precipitates were filtered, washed with water, and recrystallized from DMF-water to give yellowish crystals (320 mg, yield 41%) of N-(2-methyl-4-thiazolyl)-1H-tetrazole-5-carboxamide (Ia-1), m.p. 295°–297° C. (decomp).

EXAMPLE 2

N-(2-(4-Methylphenyl)-4-thiazolyl)-1H-tetrazole-5-carboxamide (Ia-5) (Process b)

A mixture, obtained by adding ice-cooled dry DMF(0.53 ml, 6.48 mmol) and then thionyl chloride (0.499 ml, 6.84 mmol) to dry benzene (1.5 ml,, was allowed to warm up to room temperature and to react for 10 minutes upon which the mixture separated into two layers. The lower layer was added dropwise to dipotassium salt of 1H-tetrazole-5-carboxylic acid (867 mg, 4.56 mmol) suspended in dry acetonitrile (15 ml) under ice-cooling. The mixture was allowed to react for 15 minutes. After adding dropwise a mixed solution of 2-(4-methylphenyl)-4-thiazolamine (928 mg, 4.88 mmol) in dry acetonitrile (15 ml) and dry pyridine (4 ml) under the same conditions, the mixture was allowed to warm up to room temperature and to react for 1 hour. After dissolution was effected with addition of water, the reaction mixture was acidified under ice-cooling with 2N-HCl to pH 2. The deposited solids were filtered with suction, washed with water and recrystallized from methanol-water to give yellowish crystals (677 mg. yield 52%) of N-(2-(4-methylphenyl)-4-thiazolyl)-1H-tetrazole-5-carboxamide (Ia-5), m.p.228°–230° C.

EXAMPLE 3

N-(2-(3-Pyridyl)-4-thiazolyl)-1H-tetrazole-5-carboxamide (Ia-23) (Process b)

A mixture, obtained oy adding dry DMF (0.197 ml, 2.63 mmol) and then thionyl chloride (0.192 ml, 2.63 mmol) to dry benzene (1 ml) under ice-cooling, was allowed to warm up to room temperature and to react for 10 minutes upon which the mixture separated into two layers. The lower layer was added dropwise to dipotassium salt of 1H-tetrazole-5-carboxylic acid (333 mg, 1.75 mmol) suspended in dry acetonitrile (5 ml) under ice-cooling. The mixture was allowed to react for 15 minutes. After adding dropwise a mixed solution of 2-(3-pyridyl)4-thiazolamine (330 mg, 1.86 mmol) in dry acetonitrile (3 ml) and dry pyridine (1 ml) under the same conditions, the mixture was allowed to warm up to room temperature and to react for 1 hour. After dissolution was effected with addition of water, the reaction mixture was neutralized under ice-cooling with 2N-HCl to pH 7. The deposited solids were filtered with suction, was recrystallized from methanol-THF-water to give yellow crystals (181 mg, yield 38%) of N-(2-(3-pyridyl)-4-thiazolyl)-1H-tetrazole-5-carboxamide (Ia-23), m.p. 263°-265° C.

EXAMPLE 4

N-(2-(4-Methylphenyl)-4-thiazolyl)-1H-tetrazole-5-carboxamide monosodium salt (Ia-5′)

To a suspension of N-(2-(4-methylphenyl)-4-thiazolyl)-1H-tetrazole-5-carboxamide (Ia-5) (100 mg, 0.35 mmol) in water (5 ml) was added dropwise 0.1 N aqueous sodium hydroxide (3.5 ml, 0.35 mmol) and the mixture was allowed to react at room temperature for 30 minutes. The insoluble matters in the reaction mixture was removed by filtration and the solvent was distilled off from the filtrate. The residue was crystallized by adding dry acetone, filtered with suction and dried to give pale yellow solids of N-(2-(4-methylphenyl)-4-thiazolyl)-1H-tetrazole-5-carboxamide monosodium (Ia-5′) (72 mg, yield 67%), m.p. above 300° C.

EXAMPLE 5

N-(2-(4-Methylphenyl)-4-thiazolyl)-1H-tetrazole-5-carboxamide 2-aminoethanol salt (Ia-5″)

To N-(2-(4-methylphenyl)-4-thiazolyl)-1H-tetrazole-5-carboxamide (Ia-5) (100 mg, 0.35 mmol) dissolved in dry methanol (10 ml) was added dropwise 2-aminoethanol (0.23 ml, 0.39 mmol) and the mixture was allowed to react at room temperature for 30 minutes. The solvent was distilled off from the reaction mixture. The residue was crystallized by adding dry ether, filtered with suction and dried to give pale yellow solids of N-(2-(4-methylphenyl)-4-thiazolyl)-1H-tetrazole-5-carboxamide 2-aminoethanol salt (Ia-5″) (112 mg, yield 92%), m.p. 172°-175° C.

The following compounds (I) of the invention were prepared according to the processes described in any one of the above examples 1-3.

N-(2-phenyl-4-thiazolyl-)-1H-tetrazole-5-carboxamide (Ia-2) from 2-phenyl-4-thiazolamine, N-(2-(2-methylphenyl)-4-thiazolyl)-1H-tetrazole-5-carboxamide (Ia-3) from 2-(2-methylphenyl)-4-thiazolamine, N-(2-(3-methylphenyl)-4-thiazolyl)-1H-tetrazole-5-carboxamide (Ia-4) from 2-(3-methylphenyl)-4-thiazolamine, N-(2-(2-methoxyphenyl)-4-thiazolyl)-1H-tetrazole-5-carboxamide (Ia-6) from 2-(2-methoxyphenyl)-4thiazolamine, N-(2-(3-methoxyphenyl)-4-thiazolyl)-1H-tetrazole-5-carboxamide (Ia-7) from 2-(3-methoxyphenyl)-4-thiazolamine, N-(2-(4-methoxyphenyl)-4-thiazolyl)-1H-tetrazole-5-carboxamide (Ia-8) from 2-(4-methoxyphenyl)-4thiazolamine, N-(2-(3,5-dimethoxyphenyl)-4-thiazolyl)-1H-tetrazole-1H-tetrazole-5-carboxamide (Ia-9) from 2-(3,5-dimethoxyphenyl)-4-thiazolamine, N-(2-(3,4,5-trimethoxyphenyl)-4-thiazolyl)-1H-tetrazole-5-carboxamide (Ia-10) from 2-(3,4,5-trimethoxyphenyl)-4-thiazolamine, N-(2-(2-hydroxyphenyl)-4-thiazolyl)-1H-tetrazole-5-carboxamide (Ia-11) from 2-(2-hydroxyphenyl)-4-thiazolamine, N-(2-(2-benzyloxyphenyl)-4-thiazolyl)-1H-tetrazole-5-carboxamide (Ia-12) from 2-(2-benzyloxyphenyl)-4-thiazolamine, N-(2-(2-nitrophenyl)-4-thiazolyl)-1H-tetrazole-5-carboxamide (Ia-13) from 2-(2-nitrophenyl)-4thiazolamine, N-(2-(3-trifluoromethylphenyl)-4-thiazolyl)-1H-tetrazole-5-carboxamide (Ia-14) from 2-(3-trifluoromethylphenyl)-4-thiazolamine, N-(2-(4-chlorophenyl)-4-thiazolyl)-1H-tetrazole-5-carboxamide (Ia-15) from 2-(4 chlorophenyl)-4-thiazolamine, N-(2-(4-(1-methylethyl)phenyl)-4-thiazolyl) 1H-tetrazole-5-carboxamide (Ia-16) from 2-(4-(1-methylethyl)phenyl)-4-thiazolamine, N-(2-(4-(1,1-dimethylethyl)phenyl)-4-thiazolyl)-1H-tetrazole-5-carboxamide (Ia-17) from 2-(4-(1,1-dimethylethyl)phenyl)-4-thiazolamine, N-(2-(1-naphthyl)-4-thiazolyl)-1H-tetrazole-5-carboxamide (Ia-18) from 2-(1-naphtyl)-4-thiazolamine, N-(2-(4-methylphenyl)-5-methyl-4-thiazolyl)-1H-tetrazole-5-carboxamide (Ia-19) from 2-(4-methylphenyl)-5-methyl-4-thiazolamine, N-(2-(4-methoxyphenyl)-5-methyl-4-thiazolyl)-1H-tetrazole-5-carboxamide (Ia-20) from 2-(4-methoxyphenyl)-5-methyl-4-thiazolamine, N-(5-ethyl-2-(4-methylphenyl)-4-thiazolyl)-1H-tetrazole-5-carboxamide (Ia-21) from 5-ethyl-2-(4-methylphenyl)-4-thiazolamine, N-(5-(1-methylethyl)-2-(4-methylphenyl)-4-thiazolyl)-1H-tetrazole-5-carboxamide (Ia-22) from 5(1-methylethyl)-2-(4-methylphenyl)-4-thiazolamine, N-(2-(2-furyl)-4-thiazolyl)-1H-tetrazole-5-carboxamide (Ia-24) from 2-(2-furyl)-4-thiazolamine, N-(2-(2-thienyl)-4-thiazolyl)-1H-tetrazole-5-carboxamide (Ia-25) from 2-(2-thienyl)-4-thiazolamine, N-(2-(2-quinolyl)-4-thiazolyl)-1H-tetrazole-5-carboxamide (Ia-26) from 2-(2-quinolyl)-4-thiazolamine, N-(2-(2-furyl)-5-methyl-4-thiazolyl)-1H-tetrazole-5-carboxamide (Ia-27) from 2-(2-furyl)-5-methyl-4-thiazolamine.

The following salts were also prepared according to the procedure described in Example 5.

N-(2-(4-methoxyphenyl)-4-thiazolyl)-1H-tetrazole-5-carboxamide 2-aminoethanol salt (Ia-8′).

The starting compounds (II) and compounds of the invention prepared according to the above Preparations and Examples are shown in Tables 1 and 2.

In table 2, yields are those in the single step from the compounds (II) to the compounds (I). The yield of Ia-11 is that obtained by hydrogenation of Ia-12.

Preparation 4

4-(4-Methylphenyl)-2-thiazolamine (synthesis of starting

To a mixture of thiourea (2.18 g, 28.6 mmol) and p-methylacetophenone (1.92 ml, 14.3 mmol) was added dropwise sulfuryl chloride (1.264 ml, 15.74 mmol) and the resulting mixture was stirred at room temperature for 10 minutes (until solidification was complete). The reaction mixture was allowed to react at 105° C. for 3 hours and acetone was added thereto. Then insoluble matters were filtered with suction, treated with 300 ml of water and heated at 80° C. Insoluble solids were removed by filtration. After the filtrate was made alkaline (pH 11) with 1N-KOH under ice-cooling, the deposited solids were filtered with suction, washed with water and recrystallized from methanol-water to afford 1.46 g (yield 54%) of 4-(4-methylphenyl)-2-thiazolamine as pale yellowish crystals, m.p.130° C.

IR ($\gamma^{KBr}_{max}$, cm$^{-1}$); 3450, 330.

$^1$H-NMR (CDCl$_3$, δ); 2.33(3H, s, —CH$_3$), 5.40 (2H, brs, —NH$_2$), 6.57 (1H, s, thiazole ring $\underline{H}$), 7.10 (2H, d, benzene ring $\underline{H}$), 7.60 (2H, d, benzene ring $\underline{H}$)

Preparation 5

4-(4-Methylphenyl)-2-thiazolecarboxylic acid (synthesis of starting material)

A solution of 2-bromo4′-methylacetophenone (826 mg, 3.76 mmol) and 2-thio-oxamic acid ethyl ester (1 g, 7.51 mmol) in dry ethanol (30 ml) was heated under reflux for 1.5 hours. After distilling off the solvent from the reaction mixture, the residue was treated with water, made weak alkaline (pH=8) with saturated aqueous sodium carbonate and extracted with ethyl acetate. The organic phase was washed with saturated saline and dried over anhydrous sodium sulfate, and the solvent was distilled off. The residue was dissolved in developing solvent (n-hexane:ethyl acetate=8:2) and applied on silica gel column. The first fraction (impurities) was discarded and he following fraction (colorless solution) was pooled and concentrated to give viscous product, which was crystallized by adding n-hexane. The crystals were filtered with suction to give 438 mg.(yield 47%) of ethyl 4-(4-methylphenyl)-2-thiazolecarboxylate as white solids, m.p. 53°-57° C.

To a solution of ethyl 4-(4-methylphenyl)-2-thiazolecarboxylate (300 mg, 1.21 mmol) dissolved in methanol (10 ml) was added 1N-KOH (3.63 ml, 3.63 mmol) and the mixture was allowed to react at 60° C. for 15 minutes. After the solvent was distilled off from the reaction mixture, the residue was dissolved by adding water and acidified (pH=2) with 2N-HCl under ice-cooling. The produced precipitates were filtered with suction, washed with water and recrystallized from methanol-water to afford 190 mg (yield 72%) of the desired 4-(4-methylphenyl)-2-thiazolecarboxylic acid as white solids, m.p. 112°-114° C.

IR ($\gamma^{KBr}_{max}$, cm$^{-1}$); 1690.

$^1$H-NMR (DMSO-d$_6$, δ); 2.33 (3H, s, —CH$_3$), 7.22(2H, d, benzene ring $\underline{H}$), 7.82 (2H, d, benzene ring $\underline{H}$), 8.27(1H d, thiazole ring $\underline{H}$)

EXAMPLE 6

N-(4-(4-Methylphenyl)-2-thiazolyl)-1H-tetrazole-5-carboxamide; (Ib-5) (Process b):

To dry benzene (1 ml) was added dry DMF (0.296 ml, 3.95 mmol) and then thionyl chloride (0.288 ml, 3.95 mmol) under ice-cooling. The mixture was allowed to warm up to room temperature and to react for 10 minutes upon which the mixture separated into two layers. The lower layer was added dropwise under ice-cooling to a suspension of dipotassium 1H-tetrazole-5-carboxylate (500 mg, 2.63 mmol) in dry acetonitrile (10 ml) and allowed to react for 15 minutes. After adding a mixed solution of 4-(4-methylphenyl)-2-thiazolamine (500 mg, 2.63 mmol) in dry acetonitrile (3 ml) and dry pyridine (2 ml) under the same conditions, the mixture was allowed to warm up to room temperature and to react for 1 hour. The reaction mixture was dissolved by addition of water and acidified (pH=1) with 2N-HCl under ice-cooling. The produced precipitates were filtered with suction, suspended in 100 ml of water, made alkaline (pH=11) with 1N potassium hydroxide with heating at 60° C. and then extracted with ethyl acetate (unreacted amine removed). After acidifing the aqueous phase with 2N-HCl under ice-cooling (pH=2), the deposited solids were filtered with suction, washed with water and recrystallized from methanol-THF-water to give 271 mg (yield 36%) of pale yellow crystals of N-(4-(4-methylphenyl)-2-thiazolyl)-1H-terrazole-5-carboxamide, m.p. 250°-253° C.

EXAMPLE 7

4-(4-Methylphenyl)-N-(1H-tetrazole-5-yl)-2-thiazolecarboxamide; (Ib-13) (Process a):

A mixture of 4-(4-methylphenyl)-2-thiazolecarboxylic acid (300 mg, 1.37 mmol) and N,N -carbonyl diimidazole (CDI) (444.3 mg, 2.74 mmol) dissolved in dry DMF (5 ml) was stirred at room temperature for 1 hour. Under the same conditions, a solution of 5-aminotetrazole (139.5 mg, 1.64 mmol) in dry DMF was added thereto, and the resulting mixture was allowed to react at 85° C. for 2 hours. After removing of the solvent from the reaction mixture by distillation, the residue was treated with water and acidified with 1N-HCl to pH 2. The deposited solids were filtered with suction, washed with water and recrystallized from methanol-THF-water to give 258 mg (yield 66%) of 4-(4-methylphenyl)-N-(1H-tetrazole-5-yl)-2-thiazolecarboxamide as pale yellow crystals, m.p. 276°-278° C.

The following compounds (I) were prepared as described in any one of the above Example 6 and 7.

N-(4-phenyl-2-thiazolyl)-1H-tetrazole-5-carboxamide (Ib-1) from 4-phenyl-2-thiazolamine, N-(4-(2-methoxyphenyl)-2-thiazolyl)-1H-tetrazole-5-carboxamide (Ib-2) from 4-(2-methoxyphenyl)-2-thiazolamine, N-(4-(3-methoxyphenyl)-2-thiazolyl)-1H-tetrazole-5-carboxamide ·(Ib-3) from 4-(3-methoxyphenyl)-2-thiazolamine, N-(4-(4-methoxyphenyl;-2-thiazolyl)-1H-tetrazole-5-carboxamide (Ib-4) from 4-(4-methoxyphenyl)-2-thiazolamine, N-(4-(4-benzyloxyphenyl)2-thiazolyl)-1H-tetrazole-5-carboxamide (Ib-6) from 4-(4-benzyloxyphenyl)-2-thiazolamine, N-(4-(4-chlorophenyl)-2-thiazolyl)-1H-tetrazole-5-carboxamide (Ib-7) from 4-(4-chlorophenyl)-2-thiazolamine, N-(4-(4-nitrophenyl)-2-thiazolyl)-1H-tetrazole-5-carboxamide (Ib-8) from 4-(4-nitrophenyl)-2-thiazolamine, N-(4-(3,4-dimethoxyphenyl)-2-thiazolyl)-1H-tetrazole-5-carboxamide (Ib-9) from 4-(3,4-dimethoxyphenyl)-2-thiazolamine, N-(4-(2,3,4-trichlorophenyl)-2-thiazolyl)-1H-tetrazole-5-carboxamide (Ib-10) from 4-(2,3,4-trichlorophenyl)-2-thiazolamine, N-(4-(2-thienyl)-2-thiazolyl)-1H-tetrazole-5-carboxamide (Ib-11) from 4-(2-thienyl)-2-thiazolamine, N-(5-methyl-4-phenyl-2-thiazolyl)-1H-tetrazole-5-carboxamide (Ib-12) from 5-methyl-4-phenyl-2-thiazolamine, 4-(4-methoxyphenyl)-N (1H-tetrazole-5-yl)-2-thiazolecarboxamide (Ib-14) from 4-(4-methoxyphenyl)-2-thiazolecarboxylic acid, 5-methyl-4-phenyl-N-(1H-tetrazole-5-yl)-2-thiazolecarboxamide (Ib-15) from 5-methyl-4-phenyl-2-thiazolecarboxylic acid.

N-(4-(4-trifluoromethylphenyl)-2-thiazolyl)-1H-tetrazole-5-carboxamide (Ib-16) from 4-(4-trifluoromethylphenyl)-2-thiazolamine, N-(4-((1,1'-biphenyl)-4-yl)-2-thiazolyl)-1H-tetrazole-5-carboxamide (Ib-17) from 4-((1,1'-biphenyl)-4-yl)-2-thiazolamine, N-(4-(2-naphthyl)-2-thiazolyl)-1H-tetrazole-5-carboxamide (Ib-18) from 4-(2-naphthyl)-2-thiazolamine, N-(4-(3-pyridyl)-2-thiazolyl)-1H-tetrazole-5-carboxamide (Ib-19) from 4-(3-pyridyl)-2-thiazolamine, N-(4-(3-ethylphenyl)-2-thiazolyl)-1H-tetrazole-5-carboxamide (Ib-20) from 4-(3-ethylphenyl)-2-thiazolamine, N-(4-(3,4-dimethylphenyl)-2-thiazolyl)-1H-tetrazole-5-carboxamide (Ib-21) from 4-(3,4-dimethylphenyl)-2-thiazolamine, N-(4-(2-furyl)-2-thiazolyl)-1H-tetrazole-5-carboxamide (Ib-22) from 4-(2-furyl)-2-thiazolamine, N-(4-(5-chloro-2-thienyl)-2-thiazolyl)-1H-tetrazole-5-carboxamide (Ib-23) from 4-(5-chloro-2-thienyl)-2-thiazolamine.

The compounds (I) of the invention prepared according to the above Examples are shown in Table 3.

Preparation 6

2-(4-Methoxyphenyl)-4-methyl-5-thiazolecarboxylic acid (synthesis of starting material)

To a solution of p-methoxythiobenzamide (3 g, 17.95 mmol) dissolved in dry ethanol (180 ml) was added ethyl 2-chloroacetoacetate (1.28 ml, 8.98 mmol), and the mixture was heated under reflux for 1.5 hours. After the reaction was completed, the solvent was distilled off from the reaction mixture. Then the residue was treated with water, made weak alkali (pH=8) with saturated aqueous sodium carbonates, and extracted with ethyl acetate. The organic phase was washed with saturated saline and dried over anhydrous sodium sulfate. After removing the solvent by distillation, the residue was dissolved in chloroform (insoluble solids being filtered off) and applied on silica gel column (developing solvent:n-hexane:ethyl acetate=85:15). After discarding the first fraction (impurities), the second colorless fraction was pooled and concentrated to give 1.9 g of ethyl 2-(4-methoxyphenyl)-4-methyl-5-thiazolecarboxylate as white crystals.

This compound (1.9 g, 6.85 mmol) was dissolved in methanol (150 ml) with heating. After adding 1N-KOH (34.3 ml, 34.3 mmol), the mixture was allowed to react at 70° C. for 1.5 hours. After the reaction was completed, the solvent was distilled off from the reaction mixture. The residue was dissolved by adding water and acidified with 2N-HCl under ice-cooling to pH 2, and then the deposited solids were filtered with suction, washed with water and recrystallized from methanol-water to give 1.49. g (yield 67%) of 2-(4-methoxyphenyl)-4-methyl-5-thiazolecarboxylic acid as white crystals, m.p. 244°-245° C.

IR ($\gamma^{KBr}_{max}$, cm$^{-1}$); 3250–1950, 1675.

$^1$H-NMR (DMSO-d$_6$, δ); 2.67 (3H,s,thiazole ring —CH$_3$), 3.82 (3H,s, benzene ring —OCH$_3$), 7.00 (2H,d, benzene ring —H), 7.83 (2H,d, benzene ring —H)

Preparation 7

2-(4-Methoxyphenyl)-4-methyl-5-thiazolamine (synthesis of starting material)

After 2-(4-methoxyphenyl)-4-methyl-5-thiazolecarboxylic acid (1 g, 4.01 mmol) was suspended in dry THF (30 ml), dissolution was effected by addition of triethylamine (0.559 ml, 4.01 mmol). In an ice-salt bath, ethyl chloroformate (0.382 ml, 4.01mmol) was added dropwise of the solution and was allowed to react for 5 minutes under the same conditions. The reaction mixture was transferred to an ice bath, then a solution of sodium azide (2.61 g, 40.1 mmol) in water (15 ml) was added thereto. The mixture was allowed to react for 30 minutes under the same conditions. The reaction mixture was poured into water and extracted with ethyl acetate. The organic phase was washed with water, dried over anhydrous sodium sulfate and concentrated to give 910 mg of pale yellow solids of 2-(4-methoxyphenyl)-4- methyl-5-thiazolecarbonylazide.

This compound was dissolved in dry toluene (30 ml) under argon and allowed to react at 100° C. for 1 hour. Under the same conditions, 0.793 ml (6.64 mmol) of 2-trimethylsilylethanol was added thereto and the mixture was allowed to react for additional 1.5 hours. The solvent was distilled off from the reaction mixture, and then the residue was dissolved in benzene and applied on silica gel column (developing solvent:benzene:ethyl acetate =8:2). The pale yellow solution first eluted was collected and concentrated to form viscous residue, which was crystallized by adding n-hexane to give 1.15 g (yield 79%) of 2-trimethylsilylethyl 2-(4-methoxyphenyl)-4-methyl-5-thiazolecarboxylate as white solids, m.p. 80°-82° C.

IR ($\gamma^{KBr}_{max}$, cm$^{-1}$); 3300, 1715, 1690. $^1$H-NMR (CDCl$_3$, δ); 0.07 (9H, s, —Si(CH$_3$)$_3$, 0.67–1.23 (2H,m, —COOCH$_2$CH$_2$—), 2.32 (3H, s, —CH$_3$), 3.78(3H, s, —OCH$_3$), 4.10–4.47 (2H, m, —COOCH$_2$CH$_2$—), 6.60 (1H, brs, —NHCO—), 6.87 (2H, d, benzene ring —H), 7.73 (2H, d, benzene ring —H).

The above obtained 2-trimethylsilylethyl ester (1.15 g, 3.15 mmol) was dissolved in 1M solution of tetrabutylammonium fluoride (TBAF) in tetrahydrofuran (12.6 ml, 12.6 mmol) and allowed to react at 65° C. for two hours. After the solvent was distilled off from the reaction mixture, the residue was dissolved in ethyl acetate, washed with saturated aqueous ammonium chloride and water in turn, dried over anhydrous sodium sulfate and concentrated to give 635 mg (yield 92%) of 2-(4-methoxyphenyl)-4-methyl-5-thiazolamine as yellow solids. (The total yield obtained from 2-(4-methoxyphenyl)-4-methyl-5-thiazolecarboxylic acid is 72%.) m.p. 129°–131° C.

IR ($\gamma^{KBr}_{max}$, cm$^{-1}$); 3400, 3250.

$^1$H-NMR (CDCl$_3$, δ); 2.30 (3H, s, —C$\underline{H}_3$), 3.37 (2H, brs,
 —N$\underline{H}_2$), 3.78 (3H, s, —OC$\underline{H}_3$), 6.87 (2H, d,
 benzene ring—$\underline{H}$), 7.67 (2$\overline{H}$, d, benzene
 ring—$\underline{H}$).

EXAMPLE 8

2-(4-Methoxyphenyl)-4-methyl-N-(1H-tetrazole-5-yl)-5-thiazolecarboxamide; (Ic-6) (Process a)

A solution of 300 mg (1.20 mmol) of 2-(4-methoxyphenyl)-4-methyl-5-thiazolecarboxylic acid and 292.7 mg (1.81 mmol) of N,N'-carbonyldiimidazole (CDI) in dry dimethylformamide (8 ml) was stirred at room temperature for 1 hour. Under the same conditions, a solution of 5-aminotetrazole (122.8 mg, 1.44 mmol) in dry dimethylformamide (1 ml) was added thereto and allowed to react at 70° C. for 3 hours. After the solvent was distilled off from the reaction mixture, the residue was treated with water under ice-cooling and acidified with 2N-HCl to pH 2. The produced solids were filtered with suction, suspended in 100 ml of water and made alkaline with 1N potassium hydroxide (pH=11). After the impurities were removed from the alkaline solution by extracting with ethyl acetate, the aqueous phase was acidified with 2N-HCl to pH 2 and the deposited solids were filtered with suction, washed with water and recrystallized from methanol-THF-water to give 244.4 mg (yield 64 %) of 2-(4-methoxyphenyl)-4-methyl-N-(1H-tetrazole-5-yl)-5-thiazolecarboxamide as white crystals, m.p. 275°–278° C.

EXAMPLE 9

N-(2-(4-Methoxyphenyl)-4-methyl-5-thiazolyl)-1H-tetrazole-5-carboxamide; (Ic-14) (Process b)

To dry benzene (1 ml) was added dropwise dry dimethylformamide (0.264 ml, 3.41 mmol) and thionyl chloride (0.249 ml, 3.41 mmol) in this order under ice-cooling. The mixture was allowed to warm up to room temperature and was stirred for 10 minutes upon which the mixture separated into two phases. The lower phase was added to a suspension of dipotassium tetrazole-5-carboxylate (517.5 mg, 2.72 mmol) in dry acetonitrile (5 ml) under ice-cooling and stirred for 15 minutes. Under the same conditions, a mixed solution of 2-(4-methoxyphenyl)-4-methyl-5-thiazolamine (500 mg, 2.72 mmol) in dry acetonitrile (5 ml) and dry pyridine (2.5 ml) was added dropwise thereto and allowed to react at room temperature for 1 hour. After the reaction mixture was dissolved by addition of water under ice-cooling and acidified with 2N-HCl to pH 2, the deposited solids were filtered with suction, then suspended in 200 ml of water and made alkaline with 1N-KOH to pH 12. The impurities were removed from the alkaline solution by extracting with ethyl acetate, and the aqueous phase was acidified with 2N-HCl to pH 2 under ice-cooling. The produced solids were filtered with suction, washed with water and recrystallized from methanol-water to give 381 mg (yield 53%) of N-(2-(4-methoxyphenyl)-4-methyl-5-thiazolyl)-1H-tetrazole-5-carboxamide as yellowish crystals, m.p. 205°–207° C.

The following compounds (I) were prepared according to the processes described in the above Example 8 or 9.

4-methyl-2-phenyl-N-(1H-tetrazole-5-yl)-5-thiazolecarboxamide; (Ic-1), 4-methyl-2-(2-nitrophenyl)-N-(1H-tetrazole-5-yl)-5-thiazolecarboxamide; (Ic-2), 2-(3-methoxyphenyl)-4-methyl-N-(1H-tetrazole-5-yl)-5-thiazolecarboxamide; (Ic-3), 2-(4-chlorophenyl)-4-methyl-N-(1H-tetrazole-5-yl)-5-thiazolecarboxamide; (Ic-4), 4-methyl-2-(4-methylphenyl)-N-(1H-tetrazole-5-yl)-5-thiazolecarboxamide; (Ic-5), 2-(3,5-dimethoxyphenyl)-4-methyl-N-(1H-tetrazole-5-yl)-5-thiazolecarboxamide; (Ic-7), 4-methyl-2-(3,4,5-trimethoxyphenyl)-N-(1H-tetrazole-5-yl)-5-thiazolecarboxamide; (Ic-8), N-(4-methyl-2-phenyl-5-thiazolyl)-1H-tetrazole-5carboxamide; (Ic-9), N-(4-methyl-2-(2-nitrophenyl)-5-thiazolyl)-1H-tetrazole-5-carboxamide; (Ic-10), N-(2-(3-methoxyphenyl)-4-methyl-5-thiazolyl)-1H-tetrazole-5-carboxamide; (Ic-11), N-(2-(4-chlorophenyl)-4-methyl-5-thiazolyl)-1H-tetrazole-5-carboxamide; (Ic-12), N-(4-methyl-2-(4-methylphenyl)-5-thiazolyl)-1H-tetrazole-5-carboxamide; (Ic-13), N-(2-(3,5-dimethoxyphenyl)-4-methyl-5-thiazolyl)-1H-tetrazole-5-carboxamide;(Ic-15), N-(4-methyl-2-(3,4,5-trimethoxyphenyl)-5-thiazolyl)-1H-tetrazole-5-carboxamide; (Ic-16).

The compounds (I) of the invention prepared according to the above Examples are shown in Table 4.

| FORMULATION 1 | |
|---|---|
| (1) Active ingredient | 25.00 mg |
| (2) Lactose | 49.00 mg |
| Crystalline cellulose | 36.00 mg |
| Corn starch | 5.00 mg |
| (3) Hydroxypropyl cellulose | 1.00 mg |
| (4) ECG505 (carboxymethyl cellulose calcium) | 2.00 mg |
| (5) Magnesium stearate | 1.00 mg |
| (6) Talc | 1.00 mg |
| Total | 120 mg |

(1)+(2) were kneaded with 5% aqueous solution of (3), dried, and granulated, to which (4), (5), and (6) were added to mix together. The mixture was pressed into tablets of 120 mg each, 7 mm in diameter.

| FORMULATION 2 | |
|---|---|
| (1) Active ingredient | 50.00 mg |
| (2) Lactose | 124.50 mg |
| Corn starch | 20.00 mg |
| (3) Hydroxypropyl cellulose | 2.00 mg |
| (4) Light anhydrous silicic acid | 1.50 mg |
| (5) Magnesium stearate | 2.00 mg |
| Total | 200 mg |

(1)+(2) were kneaded with 5% aqueous solution of (4), dried, and granulated, to which (5) and (6) were added to mix together, and the mixture (200 mg) was filled in hard gelatine capsule #3.

(In the above FORMULATIONS 1 and 2, the term active ingredient means optional one of the compounds of the formula (I)0.

TEST EXAMPLE 1

Anti-passive cutaneous anaphylaxis (PCA) activity in rats (Materials and Method)

(1) Animals used

Wistar strain male rats (6 weeks old) were purchased from Shizuoka Experimental Animal Agricultural Cooperative (Japan), habituated to a breeding environment for 1 week before using for the experiment.

(2) Preparation of antiserum

Preparation of antiserum was carried out according to the method described in J. Immunol. 106, 1002–1011 (1971).

Thus, Ascaris suum extract was dinitrophenylated (DNP-As) and infused subcutaneously together with dead Bordetella pertussis at four sites on the foot-pad of the Wistar strain male rats. After 5 days, the rats were boostered with DNP-As (1 mg) at the dorsal muscle for additional sensitization. After 3 days, blood samples were collected and serum was separated which was used as anti DNP-As antiserum. The titer of the antiserum was measured by rats 48-hours PCA and found to be 1:200.

(3) 48-Hours PCA

Rats were sensitized with 35 times dilution of anti DNA-As antiserum administered at two sites in the pre-clipped right dorsal skin. After 48 hours, DNP-As (500 μg in 0.5 % Evans blue-physiological saline (1 ml) was administered into caudal vein to elicit the reaction. Then, 30 minutes later, the animals were decapitated, the dorsal skin was peeled, two sensitized areas as well as one control area were cut off and analyzed for Evans blue exudation which was used as an indivative of the reaction according to the method disclosed in Microbiol. Immunol. 22, 89–101 (1978). Thus, cut skins were treated with 1N-KOH (1 ml) and incubated at 37° C. for 16 hours to dissolve the skin tissue. A mixed solution (9 ml) of 0.6N-phosphoric acid-acetone (5: 13) was added and the mixture was centrifuged (300 r.p.m.) for 15 minutes. The supernatant was assayed for absorption at 620 nm and the exudation of Evans blue was determined. Test compounds (I) of the present invention were administered perorally as a suspension in 0.5% tragacanth 1 hour before the elicitation.

(Results)

The obtained results are shown in the following Tables from which it can be clearly seen that the compounds of the invention inhibit significantly the reaction and hence have a potent anti-PCA activity.

| Compound No. | Dose (mg/kg) | Inhibition (%) |
|---|---|---|
| Ia-1 | 15 | 60 |
| Ia-3 | 15 | 78 |
| Ia-4 | 15 | 39 |
| Ia-5 | 25 | 90 |
| Ia-15 | 15 | 50 |
| Ia-16 | 15 | 46 |
| Ia-17 | 15 | 47 |
| Ia-19 | 25 | 61 |
| Ia-8 | 15 | 80 |
| Ia-23 | 15 | 40 |
| Ia-25 | 15 | 43 |
| Ia-26 | 15 | 42 |
| Tranilast | 50 | 0 |

TEST EXAMPLE 2

Anti-passive cutaneous anaphylaxis (PCA) activity in rats (Materials and Method)

(1) Animals used

Wistar strain male rats (6 weeks old) were purchased from Shizuoka Experimental Animal Agricultural Cooperative (Japan), habituated to a breeding environment for 1 week before using for the experiment.

(2) Preparation of antiserum

Preparation of antiserum was carried out according to the method described in J. Immunol. 106, 1002–1011 (1971).

Thus, Ascaris suum extract was dinitrophenylated (DNP-As) and infused subcutaneously together with dead Bordetella pertussis at four sites on the foot-pad of the Wistar strain male rats. After 5 days, the rats were boostered with DNP-As (1 mg) at the dorsal muscle for additional sensitization. After 3 days, blood samples were collected and serum was separated which was used as anti DNP-As antiserum. The titer of the antiserum was measured by rats 48-hours PCA and found to be 1:200.

(3) 48-Hours PCA

Rats were sensitized with 35 times dilution of anti DNA-As antiserum administered at two sites in the pre-clipped right dorsal skin. After 48 hours, DNP-As (500 μg in 0.5% Evans blue-physiological saline (1 ml) was administered into caudal vein to elicit the reaction. Then, 30 minutes later, the animals were decapitated, the dorsal skin was peeled, two sensitized areas as well as one control area were cut off and analyzed for Evans blue exudation which was used as an indivative of the reaction according to the method disclosed in Microbiol. Immunol. 22, 89–101 (1978). Thus, cut skins were treated with 1N-KOH (1 ml) and incubated at 37° C. for 16 hours to dissolve the skin tissue. A mixed solution (9 ml) of 0.6N-phosphoric acid-acetone (5: 13) was added and the mixture was centrifuged (300 r.p.m.) for 15 minutes. The supernatant was assayed for absorption at 620 nm and the exudation of Evans blue was determined. Test compounds (I) of the present invention were administered perorally as a suspension in 0.5% tragacanth 1 hour before the elicitation.

(Results)

The obtained results are shown in the following Tables from which it can be clearly seen that the compounds of the invention inhibit significantly the reaction and hence have a potent anti-PCA activity. P.O.

| | P.O. | |
|---|---|---|
| Compound No. | Dose (mg/kg) | Inhibition (%) |
| Ib-1 | 20 | 66 |
| Ib-4 | 20 | 92 |
| Ib-5 | 20 | 89 |
| Ib-7 | 20 | 70 |
| Ib-12 | 20 | 51 |
| Ib-13 | 30 | 60 |
| Ib-14 | 30 | 50 |
| Tranilast | 50 | 0 |

TEST EXAMPLE 3

Anti-passive cutaneous anaphylaxis (PCA) activity in rats (Materials and Method)

(1) Animals used

Wistar strain male rats (6 weeks old) were purchased from Shizuoka Experimental Animal Agricultural Cooperative (Japan), habituated to a breeding environment for 1 week before using for the experiment.

(2) Preparation of antiserum

Preparation of antiserum was carried out according to the method described in J. Immunol. 106, 1002–1011 (1971).

Thus, Ascaris suum extract was dinitrophenylated (DNP-As) and infused subcutaneously together with dead Bordetella pertussis at four sites on the foot-pad of the Wistar strain male rats. After 5 days, the rats were boostered with DNP-As (1 mg) at the dorsal muscle for additional sensitization. After 3 days, blood samples were collected and serum was separated which was used as anti DNP-As antiserum. The titer of the antiserum was measured by rats 48-hours PCA and found to be 1:200.

(3) 48-Hours PCA

Rats were sensitized with 35 times dilution of anti DNA-As antiserum administered at two sites in the pre-clipped right dorsal skin. After 48 hours, DNP-As (500 μg in 0.5% Evans blue-physiological saline (1 ml) was administered into caudal vein to elicit the reaction. Then, 30 minutes later, the animals were decapitated, the dorsal skin was peeled, two sensitized areas as well as one control area were cut off and analyzed for Evans blue exudation which was used as an indivative of the reaction according to the method disclosed in Microbiol. Immunol. 22, 89–101 (1978). Thus, cut skins were treated with (1 mil) incubated at 37° C. for 16 hours to dissolve the skin tissue. A mixed solution (9 ml) of 0.6 N-phosphoric acid-acetone (5: 13) was added and the mixture was centrifuged (300 r.p.m.) for 15 minutes. The supernatant was assayed for absorption at 620 nm and the exudation of Evans blue was determined. Test compounds (I) of the present invention were administered perorally as a suspension in 0.5% tragacanth 1 hour before the elicitation.

(Results)

The obtained results are shown in the following Tables from which it can be clearly seen that the compounds of the invention inhibit significantly the reaction and hence have a potent anti-PCA activity.

| Compound No. | P.O. Dose (mg/kg) | Inhibition (%) |
|---|---|---|
| Ic-5 | 30 | 49 |
| Ic-6 | 30 | 56 |
| Ic-13 | 30 | 52 |
| Ic-14 | 30 | 50 |
| Tranilast | 50 | 0 |

TABLE 1

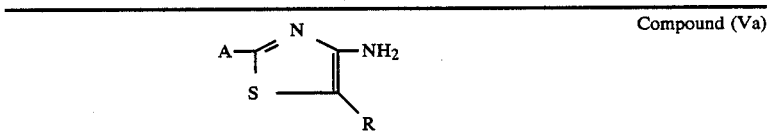

Compound (Va)

| Compound No. | A | R | m.p. (°C.) | IR (KBr, cm$^{-1}$) |
|---|---|---|---|---|
| Va-1 | methyl | H | oil | 3400, 3300 1620 |
| Va-2 | phenyl | H | 49–53 | 3400, 3300 1535 |
| Va-3 | 2-methylphenyl | H | oil | 3450, 3350 |
| Va-4 | 3-methylphenyl | H | 72–74 | 3350, 3200 |
| Va-5 | 4-methylphenyl | H | 100–102 | 3400, 3300 3200, 1630 |
| Va-6 | 2-methoxyphenyl | H | oil | 3450, 3350 1605 |
| Va-7 | 3-methoxyphenyl | H | oil | 3450, 3300 1730 |
| Va-8 | 4-methoxyphenyl | H | 113–114 | 3400, 3250 1600 |
| Va-9 | 3,5-dimethoxyphenyl | H | 80–82 | 3350, 3200 1610 |
| Va-10 | 3,4,5-trimethoxyphenyl | H | 121–123 | 3450, 3350 1610 |
| Va-11 | 2-hydroxyphenyl | H | — | — |
| Va-12 | 2-benzyloxyphenyl | H | oil | 3450, 3350 |
| Va-13 | 2-nitrophenyl | H | 99–102 | 3450, 3350 1610 |
| Va-14 | 3-trifluoromethylphenyl | H | 55–57 | 3350, 3200 1610 |
| Va-15 | 4-chlorophenyl | H | 102–104 | 3400, 3300 3200, 1630 |
| Va-16 | 4-(1-methylethyl)-phenyl | H | 69–70 | 3400, 3300 |
| Va-17 | 4-(1,1-dimethylethyl)-phenyl | H | 60–61 | 3420, 3320 1730 |
| Va-18 | 1-naphtyl | H | 105–107 | 3430, 3280 3200, 1620 |
| Va-19 | 4-methylphenyl | methyl | 129–131 | 3400, 3300 1630 |

TABLE 1-continued

Compound (Va)

A–C(=N)–S–C(R)=C(NH2)–

| Compound No. | A | R | m.p. (°C.) | IR (KBr, cm$^{-1}$) |
|---|---|---|---|---|
| Va-20 | 4-methoxyphenyl | methyl | 109–111 | 3350, 3300 1610 |
| Va-21 | 4-methylphenyl | ethyl | 48–50 | 3350, 3300 |
| Va-22 | 4-methylphenyl | 1-methylethyl | oil | 3450, 3350 |
| Va-23 | 3-pyridyl | H | 71–73 | 3300, 3200 1730 |
| Va-24 | 2-furyl | H | 95–98 | 3380, 3280 1620 |
| Va-25 | 2-thienyl | H | 98–100 | 3400, 3260 1620 |
| Va-26 | 2-quinolyl | H | 161–163 | 3400, 3300 |
| Va-27 | 2-furyl | methyl | 114–115 | 3350, 3300 |

TABLE 2

Compound (Ia)

| Compound No. | A | R | Yield (%) | m.p. (°C.) | formula M.W. | MS (m/z) | IR (KBr, cm$^{-1}$) |
|---|---|---|---|---|---|---|---|
| Ia-1 | methyl | H | 41 | 295–297 | $C_6H_6N_6OS$ 210.22 | 210(M$^+$) 140(BP) | 3300, 3150 1670 |
| Ia-2 | phenyl | H | 43 | 209–213 | $C_{11}H_8N_6OS$ 272.29 | 272(M$^+$) 202(BP) | 1690 |
| Ia-3 | 2-methylphenyl | H | 39 | 197–199 | $C_{12}H_{10}N_6OS$ 286.32 | 286(M$^+$) 216(BP) | 3275 1680 |
| Ia-4 | 3-methylphenyl | H | 42 | 209–211 | $C_{12}H_{10}N_6OS$ 286.32 | 286(M$^+$) 216(BP) | 3300 1670 |
| Ia-5 | 4-methylphenyl | H | 52 | 228–230 | $C_{12}H_{10}N_6OS$ 286.32 | 286(M$^+$) 216(BP) | 3300, 3150 1700 |
| Ia-5' | 4-methylphenyl (sodium salt) | H | 67 | above 300 | | | 3700–2500 1680, 1510 |
| Ia-5'' | 4-methylphenyl (2-aminoethanol salt) | H | 92 | 172–175 | | | 1680 |
| Ia-6 | 2-methoxyphenyl | H | 37 | 192–195 | $C_{12}H_{10}N_6O_2S$ 302.32 | 302(M$^+$) 232(BP) | 1700 |
| Ia-7 | 3-methoxyphenyl | H | 60 | 216–218 | $C_{12}H_{10}N_6O_2S$ 302.32 | 302(M$^+$) 232(BP) | 3350 1710 |
| Ia-8 | 4-methoxyphenyl | H | 55 | 249–251 | $C_{12}H_{10}N_6O_2S$ 302.32 | 302(M$^+$) 232(BP) | 3300, 3150 1710 |
| Ia-8' | 4-methoxylphenyl (2-aminoethanol salt) | H | 85 | 156–158 | — | — | 1660 |
| Ia-9 | 3,5-dimethoxyphenyl | H | 71 | 244–246 | $C_{13}H_{12}N_6O_3S$ 332.34 | 332(M$^+$) 262(BP) | 3350, 3150 1710 |
| Ia-10 | 3,4,5-trimethoxyphenyl | H | 35 | 253–255 | $C_{14}H_{14}N_6O_4S$ 362.37 | 362(M$^+$) 362(BP) | 3400, 3150 1710 |
| Ia-11 | 2-hydroxyphenyl | H | 59 | 259–261 | $C_{11}H_8N_6O_2S$ 288.29 | 288(M$^+$) 218(BP) | 1660 |
| Ia-12 | 2-benzyloxyphenyl | H | 58 | 213–215 | $C_{18}H_{14}N_6O_2S$ 378.42 | 378(M$^+$) 91(BP) | 3400 1680 |
| Ia-13 | 2-nitrophenyl | H | 44 | 225–228 | $C_{11}H_7N_7O_3S$ 317.29 | 317(M$^+$) 104(BP) | 3400 1680 |
| Ia-14 | 3-trifluoromethylphenyl | H | 43 | 197–198 | $C_{12}H_7F_3N_6OS$ 340.29 | 340(M$^+$) 270(BP) | 3300 1670 |
| Ia-15 | 4-chlorophenyl | H | 43 | 263–265 | $C_{11}H_7ClN_6OS$ 306.74 | 306(M$^+$) 236(BP) | 1680 |
| Ia-16 | 4-(1-methylethyl)phenyl | H | 25 | 185–186 | $C_{14}H_{14}N_6OS$ 314.37 | 314(M$^+$) 244(BP) | 3250 1670 |
| Ia-17 | 4-(1,1-dimethylethyl)phenyl | H | 26 | 199–202 | $C_{15}H_{16}N_6OS$ 328.40 | 328(M$^+$) 243(BP) | 3270 1670 |
| Ia-18 | 1-naphtyl | H | 48 | 231–233 | $C_{15}H_{10}N_6OS$ 322.35 | 322(M$^+$) 252(BP) | 3290 1670 |
| Ia-19 | 4-methylphenyl | methyl | 49 | 233–235 | $C_{13}H_{12}N_6OS$ 300.34 | 300(M$^+$) 230(BP) | 1680 |
| Ia-20 | 4-methoxyphenyl | methyl | 48 | 219–222 | $C_{13}H_{12}N_6O_2S$ 316.34 | 316(M$^+$) 246(BP) | 1680 1660 |

TABLE 2-continued

Compound (Ia)

| Compound No. | A | R | Yield (%) | m.p. (°C.) | formula M.W. | MS (m/z) | IR (KBr, cm$^{-1}$) |
|---|---|---|---|---|---|---|---|
| Ia-21 | 4-methylphenyl | ethyl | 61 | 248–250 | $C_{14}H_{14}N_6OS$ 314.37 | 314(M$^+$) 244(BP) | 3250 1690 |
| Ia-22 | 4-methylphenyl | 1-methylethyl | 41 | 227–229 | $C_{15}H_{16}N_6OS$ 328.40 | 328(M$^+$) 243(BP) | 3250 1690 |
| Ia-23 | 3-pyridyl | H | 38 | 263–265 | $C_{10}H_7N_7OS$ 273.28 | 273(M$^+$) 203(BP) | 1690 |
| Ia-24 | 2-furyl | H | 51 | 273–275 | $C_9H_6N_6O_2S$ 262.25 | 262(M$^+$) 192(BP) | 3220, 3160 1670 |
| Ia-25 | 2-thienyl | H | 33 | 236–238 | $C_9H_6N_6OS_2$ 278.32 | 278(M$^+$) 208(BP) | 3320 1710 |
| Ia-26 | 2-quinolyl | H | 50 | 260–261 | $C_{14}H_9N_7OS$ 323.34 | 323(M$^+$) 253(BP) | 3400 1680, 1660 |
| Ia-27 | 2-furyl | methyl | 63 | 214–216 | $C_{10}H_8N_6O_2S$ 276.28 | 276(M$^+$) 206(BP) | 1660 |

TABLE 3

Compound (Ib)

| Compound No. | A | X | Y | R | Yield (%) | m.p. (°C.) | MS (m/z) | IR (KBr, cm$^{-1}$) |
|---|---|---|---|---|---|---|---|---|
| Ib-1 | phenyl | —CO— | —NH— | H | 46 | 277–279 | 202(BP) 272(M$^+$) | 1715 |
| Ib-2 | 2-methoxyphenyl | —CO— | —NH— | H | 53 | 261–262 | 131(BP) 302(M$^+$) | 1715 |
| Ib-3 | 3-methoxyphenyl | —CO— | —NH— | H | 42 | 258–260 | 232(BP) 302(M$^+$) | 1710 |
| Ib-4 | 4-methoxyphenyl | —CO— | —NH— | H | 42 | 272–274 | 44(BP) 302(M$^+$) | 1700 |
| Ib-5 | 4-methylphenyl | —CO— | —NH— | H | 36 | 250–253 | 216(BP) 286(M$^+$) | 1700 |
| Ib-6 | 4-benzyloxyphenyl | —CO— | —NH— | H | 52 | 246–248 | 91(BP) 378(M$^+$) | 1700 |
| Ib-7 | 3-chlorophenyl | —CO— | —NH— | H | 35 | 267–270 | 236(BP) 306(M$^+$) | 1710 |
| Ib-8 | 4-nitrophenyl | —CO— | —NH— | H | 31 | 268–271 | 247(BP) 317(M$^+$) | 1680 |
| Ib-9 | 3,4-dimetoxyphenyl | —CO— | —NH— | H | 23 | 268–270 | 262(BP) 332(M$^+$) | 1700 |
| Ib-10 | 2,3,4-trichlorophenyl | —CO— | —NH— | H | 64 | 257–259 | 306(BP) 376(M$^+$) | 1690 |
| Ib-11 | 2-thienyl | —CO— | —NH— | H | 26 | 258–260 | 208(BP) 278(M$^+$) | 1700 |
| Ib-12 | phenyl | —CO— | —NH— | CH$_3$ | 37 | 278–279 | 216(BP) 286(M$^+$) | 1695 |
| Ib-13 | 4-methylphenyl | —NH— | —CO— | H | 66 | 276–278 | 116(BP) 286(M$^+$) | 3250 1690 |
| Ib-14 | 4-methoxyphenyl | —NH— | —CO— | H | 30 | 276–278 | 132(BP) 302(M$^+$) | 3250 1690 |
| Ib-15 | phenyl | —NH— | —CO— | CH$_3$ | 42 | 296–298 | 116(BP) 286(M$^+$) | 3250 1690 |
| Ib-16 | 4-trifluoromethylphenyl | —CO— | —NH— | H | 24.9 | 254–256 | 270(BP) 340(M$^+$) | 1700 |
| Ib-17 | 1,1'-biphenyl-4-yl | —CO— | —NH— | H | 57.7 | 272–275 | 278(BP) 348(M$^+$) | 1690 |
| Ib-18 | 2-naphtyl | —CO— | —NH— | H | 27.2 | 273–274 | 44(BP) 322(M$^+$) | 1700 |
| Ib-19 | 3-pyridyl | —CO— | —NH— | H | (57.2) | 286–288 | 28(BP) 273(M$^+$) | 1690 |
| Ib-20 | 3-ethylphenyl | —CO— | —NH— | H | 71.4 | 256–258 | 230(BP) 300(M$^+$) | 1700 |
| Ib-21 | 3,4-dimethylphenyl | —CO— | —NH— | H | 32.7 | 270–274 | 230(BP) 300(M$^+$) | 1700 |
| Ib-22 | 2-furyl | —CO— | —NH— | H | 63.4 | 268–269 | 192(BP) 262(M$^+$) | 3250 1700 |
| Ib-23 | 5-chrolo-2- | —CO— | —NH— | H | 47.2 | 255–257 | 44(BP) | 3250 |

TABLE 3-continued

Compound (Ib)

| Compound No. | A | X | Y | R | Yield (%) | m.p. (°C.) | MS (m/z) | IR (KBr, cm⁻¹) |
|---|---|---|---|---|---|---|---|---|
| | thienyl | | | | | | 312(M⁺) | 1700 |

TABLE 4

Compound (Ic)

| Compound No. | A | X | Y | R | Yield (%) | m.p. (°C.) | MS (m/z) | IR (KBr, cm⁻¹) |
|---|---|---|---|---|---|---|---|---|
| Ic-1 | phenyl | —CO— | —NH— | $CH_3$ | 40 | 267–269 | 202(BP) 286(M⁺) | 3350 1670 |
| Ic-2 | 2-nitrophenyl | —CO— | —NH— | $CH_3$ | 49 | 255–257 | 247(BP) 331(M⁺) | 3200 1675 |
| Ic-3 | 3-methoxyphenyl | —CO— | —NH— | $CH_3$ | 46 | 271–272 | 71(BP) 316(M⁺) | 3350 1660 |
| Ic-4 | 4-chlorophenyl | —CO— | —NH— | $CH_3$ | 45 | 274–276 | 71(BP) 320(M⁺) | 3350 1675 |
| Ic-5 | 4-methylphenyl | —CO— | —NH— | $CH_3$ | 56 | 275–278 | 71(BP) 300(M⁺) | 3200 1675 |
| Ic-6 | 4-methoxyphenyl | —CO— | —NH— | $CH_3$ | 64 | 275–278 | 71(BP) 316(M⁺) | 3200 1675 |
| Ic-7 | 3,5-dimethoxyphenyl | —CO— | —NH— | $CH_3$ | 56 | 276–278 | 44(BP) 346(M⁺) | 1675 |
| Ic-8 | 3,4,5-trimethoxyphenyl | —CO— | —NH— | $CH_3$ | 66 | 280–282 | 292(BP) 376(M⁺) | 1670 |
| Ic-9 | phenyl | —NH— | —CO— | $CH_3$ | 35 | 262–254 | 216(BP) 286(M⁺) | 3375 1680 |
| Ic-10 | 2-nitrophenyl | —NH— | —CO— | $CH_3$ | 37 | 243–245 | 134(BP) 331(M⁺) | 3300, 1670 1520, 1370 |
| Ic-11 | 3-methoxyphenyl | —NH— | —CO— | $CH_3$ | 34 | 204–205 | 246(BP) 316(M⁺) | 1680 |
| Ic-12 | 4-chlorophenyl | —NH— | —CO— | $CH_3$ | 32 | 257–259 | 250(BP) 316(M⁺) | 1690 |
| Ic-13 | 4-methylphenyl | —NH— | —CO— | $CH_3$ | 32 | 208–210 | 230(BP) 300(M⁺) | 1690 |
| Ic-14 | 4-methoxyphenyl | —NH— | —CO— | $CH_3$ | 53 | 205–207 | 246(BP) 316(M⁺) | 1680 |
| Ic-15 | 3,5-dimethoxyphenyl | —NH— | —CO— | $CH_3$ | 31 | 209–211 | 276(BP) 346(M⁺) | 1675 |
| Ic-16 | 3,4,5-trimethoxyphenyl | —NH— | —CO— | $CH_3$ | 28 | 212–213 | 306(BP) 376(M⁺) | 1640 |

| Compound No. | ¹H-NMR(DMSO-d₆)δ |
|---|---|
| Ia-1 | 2.65(3H, s, C$\underline{H}_3$—), 7.57(1H, s, thiazole-H), 11.75(1H, brs, —N$\underline{H}$CO—) |
| Ia-2 | 7.37–8.17(5H, m, Ar—$\underline{H}$), 7.87(1H, s, thiazole-$\underline{H}$), 11.83(1H, brs, —N$\underline{H}$CO—) |
| Ia-3 | 2.63(3H, s, C$\underline{H}_3$—Ph), 7.30–7.50(3H, m, Ar—$\underline{H}$), 7.63–8.07(1H, m, Ar—$\underline{H}$), 7.90(1H, s, thiazole-$\underline{H}$), 12.02(1H, brs, —N$\underline{H}$CO—) |
| Ia-4 | 2.38(3H, s, C$\underline{H}_3$—Ph), 7.17–7.93(4H, m, Ar—$\underline{H}$), 7.82(1H, s, thiazole-$\underline{H}$), 11.93(1H, brs, —N$\underline{H}$CO—) |
| Ia-5 | 2.37(3H, s, C$\underline{H}_3$—Ph), 7.27(2H, d, Ar—$\underline{H}$), 7.73(1H, s, thiazole-$\underline{H}$), 7.75(2H, d, Ar—$\underline{H}$), 11.92(1H, brs, —N$\underline{H}$CO—) |
| Ia-6 | 4.05(3H, s, C$\underline{H}_3$O—Ph), 6.20–7.77(3H, m, Ar—$\underline{H}$), 7.82(1H, s, thiazole-$\underline{H}$), 8.25(1H, dd, Ar—$\underline{H}$), 11.82(1H, brs, —N$\underline{H}$CO—) |
| Ia-7 | 3.85(3H, s, C$\underline{H}_3$O—Ph), 6.90–7.67(4H, m, Ar—$\underline{H}$), 7.83(1H, s, thiazole-$\underline{H}$), 11.97(1H, brs, —N$\underline{H}$CO—) |

| Compound No. | $^1$H-NMR(DMSO-$d_6$)δ |
|---|---|
| Ia-8 | 3.82(3H, s, C$\underline{H}_3$O—Ph), 7.00(2H, d, Ar—$\underline{H}$), 7.83(1H, s, thiazole-$\underline{H}$), 11.85(1H, brs, —N$\underline{H}$CO—) |
| Ia-9 | 3.83(6H, s, C$\underline{H}_3$O-X2), 6.53–6.70(1H, m, Ar—$\underline{H}$), 7.02(2H, d, Ar—$\underline{H}$), 7.82(1H, s, thiazole-$\underline{H}$), 11.93(1H, brs, —N$\underline{H}$CO—) |
| Ia-10 | 3.72(3H, s, 4-position C$\underline{H}_3$O—), 3.87(3H, s, 3, 5-positions C$\underline{H}_3$O—), 7.15(2H, s, Ar—$\underline{H}$), 7.75(1H, s, thiazole-$\underline{H}$), 11.92(1H, brs, —N$\underline{H}$CO—) |
| Ia-11 | 6.73–8.13(4H, m, Ar—$\underline{H}$), 7.67(1H, s, thiazole-$\underline{H}$), 11.05(1H, brs, —O$\underline{H}$), 11.47(1H, brs, —N$\underline{H}$CO) |
| Ia-12 | 5.38(2H, s, C$\underline{H}_2$—Ph), 6.17–7.72(8H, m, Ar—$\underline{H}$), 7.77(1H, s, thiazole-$\underline{H}$), 8.25(1H, dd, Ar—$\underline{H}$), 11.80(1H, brs, —N$\underline{H}$CO—) |
| Ia-13 | 7.58–8.12(4H, m, Ar—$\underline{H}$), 7.95(1H, s, thiazole-$\underline{H}$), 12.07(1H, brs, —N$\underline{H}$CO—) |
| Ia-14 | 7.53–8.43(4H, m, Ar—$\underline{H}$), 7.90(1H, s, thiazole-$\underline{H}$), 12.08(1H, brs, —N$\underline{H}$CO—) |
| Ia-15 | 7.51(2H, d, Ar—$\underline{H}$), 7.83(1H, s, thiazole-$\underline{H}$), 7.91(2H, d, Ar—$\underline{H}$), 11.98(1H, brs, —N$\underline{H}$CO—) |
| Ia-16 | 1.22(6H, d, (C$\underline{H}_3$)$_2$CH—), 2.97(1H, septet, (CH$_3$)$_2$C$\underline{H}$—), 7.30(2H, d, Ar—$\underline{H}$), 7.75(1H, s, thiazole-$\underline{H}$), 11.85(1H, brs, —N$\underline{H}$CO—) |
| Ia-17 | 1.33(9H, s, (C$\underline{H}_3$)$_3$C—), 7.53(2H, d, Ar—$\underline{H}$), 7.85(1H, s, thiazole-$\underline{H}$), 7.93(2H, d, Ar—$\underline{H}$), 11.88(1H, brs, —N$\underline{H}$CO—) |
| Ia-18 | 7.37–9.23(7H, m, naphthalene-$\underline{H}$), 7.95(1H, s, thiazole-$\underline{H}$), 12.23(1H, brs, —N$\underline{H}$CO—) |
| Ia-19 | 2.35(6H, s, C$\underline{H}_3$—Ph, thiazole-C$\underline{H}_3$), 7.23(2H, d, Ar—$\underline{H}$), 7.70(2H, d, Ar—$\underline{H}$), 11.30(1H, brs, —N$\underline{H}$CO—) |
| Ia-20 | 2.32(3H, s, thiazole-C$\underline{H}_3$), 3.80(3H, s, C$\underline{H}_3$O—Ph), 6.98(2H, d, Ar—$\underline{H}$), 7.75(2H, d, Ar—$\underline{H}$), 11.27(1H, brs, —N$\underline{H}$CO—) |
| Ia-21 | 1.25(3H, t, —CH$_2$—C$\underline{H}_3$), 2.35(3H, s, —C$\underline{H}_3$—Ph), 2.75(2H, q, —C$\underline{H}_2$—CH$_3$), 7.25(2H, d, Ar—$\underline{H}$), 7.73(2H, d, Ar—$\underline{H}$), 11.27(1H, brs, —N$\underline{H}$CO—) |
| Ia-22 | 1.27(6H, d, (C$\underline{H}_3$)$_2$CH—), 2.33(3H, s, —C$\underline{H}_3$—Ph), 3.20(1H, septet, (CH$_3$)$_2$C$\underline{H}$—), 7.22(2H, d, Ar—$\underline{H}$), 7.68(2H, d, Ar—$\underline{H}$), 11.23(1H, brs, —N$\underline{H}$CO—) |
| Ia-23 | 7.30–9.47(4H, m, pyridine-$\underline{H}$), 7.90(1H, s, thiazole-$\underline{H}$), 12.00(1H, s, —N$\underline{H}$CO—) |
| Ia-24 | 6.68(1H, dd, furyl-4-$\underline{H}$), 7.07(1H, d, furyl-3-$\underline{H}$), 7.80(1H, s, thiazole-$\underline{H}$), 7.85(1H, d, furyl-5-$\underline{H}$), |
| Ia-25 | 12.03(1H, brs, —N$\underline{H}$CO—) 7.12(1H, t, thienyl-4-$\underline{H}$), 7.53–7.90(2H, m, thienyl-3-$\underline{H}$, 5-$\underline{H}$), 7.73(1H, s, thiazole-$\underline{H}$), 12.00(1H, brs, —N$\underline{H}$CO—) |
| Ia-26 | 7.53–8.67(7H, m, quinoline-$\underline{H}$, thiazole $\underline{H}$), 12.03(1H, brs, —N$\underline{H}$CO—) |
| Ia-27 | 2.35(3H, s, thiazole-C$\underline{H}_3$), 6.62(1H, dd, furyl-4-$\underline{H}$), 6.98(1H, d, furyl-3-$\underline{H}$), 7.78(1H, brs, furyl-5-$\underline{H}$), 11.30(1H, brs, —CON$\underline{H}$—) |
| Ib-1 | 7.20–8.13(5H, m, Ar—$\underline{H}$), 7.72(1H, s, thiazole-$\underline{H}$), 10.37–11.63(1H, brs, —CON$\underline{H}$—) |
| Ib-2 | 3.90(3H, s, OC$\underline{H}_3$—), 6.83–7.43(3H, m, Ar—$\underline{H}$), 7.73(1H, s, thiazole-$\underline{H}$), 7.93–8.23(1H, m, Ar—$\underline{H}$), 11.07–12.27(1H, brs, —CON$\underline{H}$—), |
| Ib-3 | 3.82(3H, s, OC$\underline{H}_3$), 6.67–7.67(4H, m, Ar—$\underline{H}$), 7.75(1H, s, thiazole-$\underline{H}$), 10.90–12.23(1H, brs, —CON$\underline{H}$—) |
| Ib-4 | 3.77(3H, s, OC$\underline{H}_3$—), 6.94(2H, d, Ar—$\underline{H}$), 7.53(1H, s, thiazole-$\underline{H}$), 7.81(2H, d, Ar—$\underline{H}$), 9.00–10.93(1H, brs, —CON$\underline{H}$—) |
| Ib-5 | 2.33(3H, s, C$\underline{H}_3$—), 7.17(2H, d, Ar—$\underline{H}$), 7.60(1H, s, thiazole-$\underline{H}$), 7.77(2H, d, Ar—$\underline{H}$), 10.70–12.03(1H, brs, —CON$\underline{H}$—) |
| Ib-6 | 5.12(2H, s, —OC$\underline{H}_2$Ph), 7.05(2H, d, Ar—$\underline{H}$), 7.20–7.50(5H, m, Ar—$\underline{H}$), 7.55(1H, s, thiazole-$\underline{H}$), 7.85(2H, d, Ar—$\underline{H}$), 8.90–10.82(1H, brs, —CON$\underline{H}$—) |
| Ib-7 | 7.43(2H, d, Ar—$\underline{H}$), 7.77(1H, s, thiazole-$\underline{H}$), 7.92(2H, d, Ar—$\underline{H}$), 10.27–12.13(1H, brs, —CON$\underline{H}$—) |
| Ib-8 | 8.08(1H, s, thiazole-$\underline{H}$), 7.68–8.82(4H, m, Ar—$\underline{H}$) Absorption of —CONH— was not observed under these conditions. |
| Ib-9 | 3.82(6H, d, —OC$\underline{H}_3$x2), 6.82–7.75(3H, m, Ar—$\underline{H}$), 7.60(1H, s, thiazole-$\underline{H}$), 8.42–10.08(1H, brs, —CON$\underline{H}$—) |
| Ib-10 | 7.23–8.23(3H, m thiazole-$\underline{H}$) Absorption of —CONH— was not observed under these conditions. |
| Ib-11 | 6.90–7.90(3H, m, thiophene-$\underline{H}$), 7.57(1H, s, thiazole-$\underline{H}$), 8.53–10.20(1H, brs, —CON$\underline{H}$—) |
| Ib-12 | 2.50(3H, s, thiazole-C$\underline{H}_3$), 7.13–7.87(5H, m, Ar—$\underline{H}$), 9.97(1H, brs, —CON$\underline{H}$—) |
| Ib-13 | 2.38(3H, s, —C$\underline{H}_3$), 7.25(2H, d, Ar—$\underline{H}$), 8.05(2H, d, Ar—$\underline{H}$), 8.42(1H, s, thiazole-$\underline{H}$), 12.95(1H, brs, —N$\underline{H}$CO—) |
| Ib-14 | 3.82(3H, s, —OC$\underline{H}_3$), 7.00(2H, d, Ar—$\underline{H}$), 8.12(2H, d, Ar—$\underline{H}$), 8.37(1H, s, thiazole-$\underline{H}$), 12.87(1H, brs, —N$\underline{H}$CO—) |

-continued

| Compound No. | $^1$H-NMR(DMSO-$d_6$)$\delta$ |
|---|---|
| Ib-15 | 2.70(3H, s, —C$\underline{H}_3$),<br>7.37–8.07(5H, m, Ar—$\underline{H}$)<br>Absorption of —CON$\underline{H}$— was not observed under these conditions. |
| Ib-16 | 7.76(2H, d, Ar—$\underline{H}$),<br>8.13(2H, d, Ar—$\underline{H}$),<br>7.97(1H, s, thiazole-$\underline{H}$)<br>Absorption of —CON$\underline{H}$— was not observed under these conditions. |
| Ib-17 | 7.17–8.17(10H, m, diphenyl-$\underline{H}$, thiazole-$\underline{H}$),<br>10.17–11.50(1H, brs, —CON$\underline{H}$—) |
| Ib-18 | 7.23–8.73(8H, m, naphthalene-$\underline{H}$, thiazole-$\underline{H}$),<br>8.73–10.67(1H, brs, —CON$\underline{H}$—) |
| Ib-20 | 1.25(3H, t, —CH$_2$C$\underline{H}_3$),<br>2.70(2H, q, —C$\underline{H}_2$CH$_3$),<br>7.07–7.93(5H, m, thiazole-$\underline{H}$, Ar—$\underline{H}$),<br>9.60–10.83(1H, brs, —CON$\underline{H}$—) |
| Ib-21 | 2.28(6H, s, —C$\underline{H}_3$x2),<br>7.17(1H, d, Ar—$\underline{H}$),<br>7.53–7.80(3H, m, Ar—$\underline{H}$, thiazole-$\underline{H}$),<br>11.10(1H, brs, —CON$\underline{H}$—) |
| Ib-22 | 6.55(1H, dd, furan-$\underline{H}_1$),<br>6.75(1H, d, furan-$\underline{H}_2$),<br>7.43(1H, s, thiazole-$\underline{H}$),<br>7.62–7.78(1H, m, furan-$\underline{H}_3$),<br>11.25(1H, brs, —CON$\underline{H}$—) |
| Ib-23 | 7.23(2H, q, thiophene-$\underline{H}$),<br>7.63(1H, s, thiazole-$\underline{H}$),<br>Absorption of —CON$\underline{H}$— was not observed under these conditions. |
| Ic-1 | 2.83(3H, s, thiazole-C$\underline{H}_3$),<br>7.37–7.70(3H, m, Ar—$\underline{H}$),<br>7.73–8.10(2H, m, Ar—$\underline{H}$) |
| Ic-2 | 2.65(3H, s, thiazole-C$\underline{H}_3$),<br>7.53–8.18(4H, m, Ar—$\underline{H}$) |
| Ic-3 | 2.72(3H, s, thiazole-C$\underline{H}_3$),<br>3.85(3H, s, Ph—OC$\underline{H}_3$),<br>6.85–7.68(4H, m, Ar—$\underline{H}$) |
| Ic-4 | 2.70(3H, s, thiazole-C$\underline{H}_3$),<br>7.53(2H, d, Ar—$\underline{H}$),<br>7.97(2H, d, Ar—$\underline{H}$) |
| Ic-5 | 2.37(3H, s, Ph-C$\underline{H}_3$),<br>2.70(3H, s, thiazole-C$\underline{H}_3$),<br>7.27(2H, d, Ar—$\underline{H}$),<br>7.80(2H, d, Ar—$\underline{H}$) |
| Ic-6 | 2.65(3H, s, thiazole-C$\underline{H}_3$),<br>3.82(3H, s, Ph—OC$\underline{H}_3$),<br>7.03(2H, d, Ar—$\underline{H}$),<br>7.88(2H, d, Ar—$\underline{H}$) |
| Ic-7 | 2.72(3H, s, thiazole-C$\underline{H}_3$),<br>3.83(6H, s, —OC$\underline{H}_3$x2),<br>6.57–6.80(1H, m, Ar—$\underline{H}$),<br>7.05(2H, d, Ar—$\underline{H}$) |
| Ic-8 | 2.70(3H, s, thiazole-C$\underline{H}_3$),<br>3.73(3H, s, 4-position —OC$\underline{H}_3$),<br>3.88(6H, s, 3, 5-positions —OC$\underline{H}_3$),<br>7.18(2H, s, Ar—$\underline{H}$) |
| Ic-9 | 2.42(3H, s, thiazole-C$\underline{H}_3$),<br>7.28–7.58(3H, m, Ar—$\underline{H}$),<br>7.72–7.95(2H, m, Ar—$\underline{H}$),<br>9.58(1H, brs, —N$\underline{H}$CO—) |
| Ic-10 | 2.47(3H, s, thiazole-C$\underline{H}_3$),<br>7.40–8.00(4H, m, Ar—$\underline{H}$),<br>11.63(1H, brs, —N$\underline{H}$CO—),<br>(in a mixture with CDCl$_3$) |
| Ic-11 | 2.43(3H, s, thiazole-C$\underline{H}_3$),<br>3.82(3H, s, Ph—OC$\underline{H}_3$),<br>6.80–7.53(4H, m, Ar—$\underline{H}$) |
| Ic-12 | 2.43(3H, s, thiazole-C$\underline{H}_3$),<br>7.47(2H, d, Ar—$\underline{H}$),<br>7.90(2H, d, Ar—$\underline{H}$) |

-continued

| Compound No. | $^1$H-NMR(DMSO-$d_6$)$\delta$ |
|---|---|
| Ic-13 | 2.32(3H, s, Ph—C$\underline{H}_3$),<br>2.38(3H, s, thiazole-C$\underline{H}_3$),<br>7.23(2H, d, Ar—$\underline{H}$),<br>7.75(2H, d, Ar—$\underline{H}$) |
| Ic-14 | 2.38(3H, s, thiazole-C$\underline{H}_3$),<br>3.77(3H, s, Ph—OC$\underline{H}_3$),<br>6.95(2H, d, Ar—$\underline{H}$),<br>7.77(2H, d, Ar—$\underline{H}$) |
| Ic-15 | 2.43(3H, s, thiazole-C$\underline{H}_3$),<br>3.83(6H, s, —OC$\underline{H}_3$x2),<br>6.50–6.68(1H, m, Ar—$\underline{H}$),<br>6.98(2H, d, Ar—$\underline{H}$) |
| Ic-16 | 2.47(3H, s, thiazole-C$\underline{H}_3$),<br>3.82(3H, s, 4-position —OC$\underline{H}_3$),<br>3.90(6H, s, 3, 5-positions —OC$\underline{H}_3$),<br>7.07(2H, s, Ar—$\underline{H}$)<br>(in a mixture with CDCl$_3$) |

What is claimed is:

1. The compound which is represented by the formula:

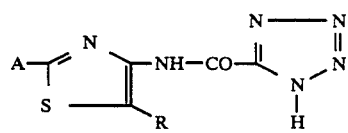

wherein
A is a $C_{1-6}$ alkyl group,
an aryl group having 6 to 10 ring carbon atoms which is unsubstituted or substituted with at least one substituent selected from the group consisting of hydroxy, $C_{1-6}$ alkoxy, aryl-($C_{1-6}$) alkoxy, halo-($C_{1-6}$) alkyl, halogen and nitro, or 5-membered heterocyclic group having from 1 to 4 ring carbon atoms containing at least one hetero atom selected from oxygen, nitrogen and sulfur, or a condensed heterocyclic group consisting of a heterocycle as defined above and benzene nucleus, or a 6-membered heterocyclic group having from 1 to 5 ring carbon atoms containing at least one hetero atom selected from oxygen, nitrogen, and sulfur, or a condensed heterocyclic group consisting of a heterocycle as defined above and a benzene nucleus,
these two heterocyclic groups being unsubstituted or substituted with at least one substituent selected from halogen,
R is hydrogen or a $C_{1-6}$ alkyl group.

2. The compound of claim 1, in which A is methyl, phenyl, methylphenyl, (1-methylethyl)phenyl, (1,1-dimethylethyl)phenyl, naphtyl, hydroxyphenyl, methoxyphenyl, dimethoxyphenyl, trimethoxyphenyl, benzyloxyphenyl, trifluoromethylphenyl, chlorophenyl, nitrophenyl, pyridyl, furyl, thienyl, or quinolyl, and
R is hydrogen, methyl or 1-methylethyl.

3. The compound which is represented by the formula:

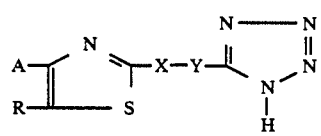

wherein A is an aryl group having from 6 to 12 ring carbon atoms which is unsubstituted or substituted with at least one substituent selected from the group consisting of $C_{1-6}$ alkoxy, aryl-$(C_{1-6})$ alkoxy, halo-$(C_{1-6})$ alkyl, halogen, and nitro, or 5-membered heterocyclic group having from 1 to 4 ring carbon atoms containing at least one hetero atom selected from oxygen, nitrogen and sulfur, or 6-membered heterocyclic groups having 1 to 5 ring carbon atoms containing at least one hetero atom selected from oxygen, nitrogen and sulfur, these two heterocyclic groups being unsubstituted or substituted with at least one substituent selected from halogen, R is hydrogen or a $C_{1-6}$ alkyl group, X is —NH—, and Y is —CO—.

4. The compound of claim 3, in which A is phenyl, methylphenyl, ethylphenyl, dimethylphenyl, biphenylyl, naphthyl, methoxyphenyl, dimethoxyphenyl, benzyloxyphenyl, chlorophenyl, trichlorophenyl, trifluoromethylphenyl, nitrophenyl, pyridyl, furyl, thienyl, or chlorothienyl, and R is hydrogen or methyl.

5. The compound which is represented by the formula:

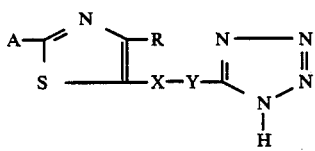

wherein

A is an aryl group having from 6 to 10 ring carbon atoms which is unsubstituted or substituted with at least one substituent selected from the group consisting of $C_{1-6}$ alkoxy, halogen and nitro, R is $C_{1-6}$ alkyl group, X is —NH—, and Y is —CO—.

6. The compound of claim 5, in which A is phenyl, methylphenyl, methoxyphenyl, dimethoxyphenyl, trimethoxyphenyl, chlorophenyl, or nitrophenyl, and R is methyl.

7. A Pharmaceutical composition comprising a therapeutically or prophylactically effective amount for the treatment of allergic diseases of at least one compound of claim 1 or a pharmaceutically acceptable salt thereof in association with a pharmaceutically acceptable carrier or diluent.

8. A Pharmaceutical composition comprising a therapeutically or prophylactically effective amount for the treatment of allergic diseases of at least one compound of claim 3 or a pharmaceutically acceptable salt thereof in association with a pharmaceutically acceptable carrier or diluent.

9. A Pharmaceutical composition comprising a therapeutically or prophylactically effective amount for the treatment of allergic diseases of at least one compound of claim 5 or a pharmaceutically acceptable salt thereof in association with a pharmaceutically acceptable carrier or diluent.

10. A method of treating allergic diseases which comprises administering a therapeutically or prophylactically effective amount of at least one compound of claim 1 or a pharmaceutically acceptable salt thereof to a subject in need of such treatment.

11. A method of treating allergic diseases which comprises administering a therapeutically or prophylactically effective amount of at least one compound of claim 3 or a pharmaceutically acceptable salt thereof to a subject in need of such treatment.

12. A method of treating allergic diseases which comprises administering a therapeutically or prophylactically effective amount of at least one compound of claim 5 or a pharmaceutically acceptable salt thereof to a subject in need of such treatment.

* * * * *

UNITED STATES PATENT AND TRADEMARK OFFICE
CERTIFICATE OF CORRECTION

PATENT NO. : 4,946,855

DATED : August 7, 1990

INVENTOR(S) : Junji Yoshinaga, et al.

It is certified that error appears in the above-identified patent and that said Letters Patent is hereby corrected as shown below:

Column 6, line 25: "compound (I)" should read as --compound (II)--

Column 9, line 19: "11.3mmol" should read as --11.36mmol--

Column 9, line 58: "6.4" should read as --6:4--

Column 11, line 6: "oy" should read as --by--

Column 11, line 64: "thiazolyl-)-" should read as --thiazolyl)- --

Column 12, lines 6, 12 & 27" "4thiazolamine" should read as --4-thiazolamine--

Column 12, line 33: "(4 chlorophenyl)" should read as --(4-chlorophenyl)--

Column 12, line 35: ") 1H-tetrazole" should read as --)-1H-tetrazole--

Column 12, line 53: "4(1-methylethyl)" should read as --5-(1-methylethyl)--

Column 13, line 10: "starting" should read as --starting material)--

Column 13, line 35: "2-bromo4'" should read as --2-bromo-4'--

Column 13, line 47: "he" should read as --the--

Column 14, line 38: "N,N" should read as --N,N'--

UNITED STATES PATENT AND TRADEMARK OFFICE
CERTIFICATE OF CORRECTION

PATENT NO. : 4,946,855

DATED : August 7, 1990

INVENTOR(S) : Junji Yoshinaga, et al.

It is certified that error appears in the above-identified patent and that said Letters Patent is hereby corrected as shown below:

Column 14, line 63: "methoxyphenyl;" should read as --methoxyphenyl)--

Column 14, line 66: ")2-thiazolyl)" should read as --)-2-thiazolyl)--

Column 15, line 18: "-N    (1H-tetrazole" should read as -- -N-(1H-tetrazole--

Column 18, line 18: "5carboxamide" should read as --5-carboxamide--

Column 18, line 62: "(1)+(2) were" should read as --(1)+(2)+(3) were--

Column 20, line 55: after "activity." delete "P.O."

Column 22, line 7: "with (1 mil)" should read as --with 1N-KOH (1 mil)--

Column 24, line 33: $C_{11}H_8H_6OS$" should read as --$C_{11}H_8N_6OS$--

Column 27, line 56: "thiazole-H)" should read as --thiazole-$\underline{H}$)--

UNITED STATES PATENT AND TRADEMARK OFFICE
CERTIFICATE OF CORRECTION

PATENT NO. : 4,946,855
DATED : August 7, 1990
INVENTOR(S) : Junji Yoshinaga, et al.

It is certified that error appears in the above-identified patent and that said Letters Patent is hereby corrected as shown below:

Column 28, line 37: "262-254" should read as --252-254--

Column 28, line 42: "316($m^+$)" should read as --320($M^+$)--

Column 30, line 23: "(3H, s, $\underline{OCH_3}$)," should read as --(3H, s, $\underline{OCH_3}$-),--

Signed and Sealed this

Eighteenth Day of February, 1992

Attest:

Attesting Officer

HARRY F. MANBECK, JR.

Commissioner of Patents and Trademarks